(12) United States Patent
Alaqel et al.

(10) Patent No.: US 11,548,850 B2
(45) Date of Patent: Jan. 10, 2023

(54) DEVELOPMENT OF A COFILIN INHIBITOR FOR THE TREATMENT OF HEMORRHAGIC BRAIN INJURY-INDUCED NEUROINFLAMMATION

(71) Applicant: The University of Toledo, Toledo, OH (US)

(72) Inventors: Saleh Alaqel, Toledo, OH (US); Viranga Tillekeratne, Toledo, OH (US); Zahoor A. Shah, Toledo, OH (US)

(73) Assignee: The University of Toledo, Toledo, OH (US)

( * ) Notice: Subject to any disclaimer, the term of this patent is extended or adjusted under 35 U.S.C. 154(b) by 239 days.

(21) Appl. No.: 16/867,100

(22) Filed: May 5, 2020

(65) Prior Publication Data
US 2020/0369603 A1    Nov. 26, 2020

Related U.S. Application Data

(60) Provisional application No. 62/851,351, filed on May 22, 2019.

(51) Int. Cl.
*C07C 275/26* (2006.01)
*A61P 25/28* (2006.01)
*C07F 7/18* (2006.01)

(52) U.S. Cl.
CPC ............ *C07C 275/26* (2013.01); *A61P 25/28* (2018.01); *C07F 7/1804* (2013.01)

(58) Field of Classification Search
CPC ............................. C07C 275/26; A61P 25/28
See application file for complete search history.

(56) References Cited

U.S. PATENT DOCUMENTS 8,912,184 B1 *  12/2014  Fleischer ............. C12Q 1/6886
514/357

\* cited by examiner

*Primary Examiner* — Shawquia Jackson
(74) *Attorney, Agent, or Firm* — MacMillan, Sobanski & Todd, LLC

(57) ABSTRACT

Compounds and methods for inhibiting cofilin activity or reducing total cofilin, improving motor deficits, attenuating LPS-induced microglial activation and inflammation, reducing microglial migration and proliferation, reducing TNF-α, reducing NF-κB, and improving motor deficits in a subject are described.

16 Claims, 27 Drawing Sheets
(21 of 27 Drawing Sheet(s) Filed in Color)

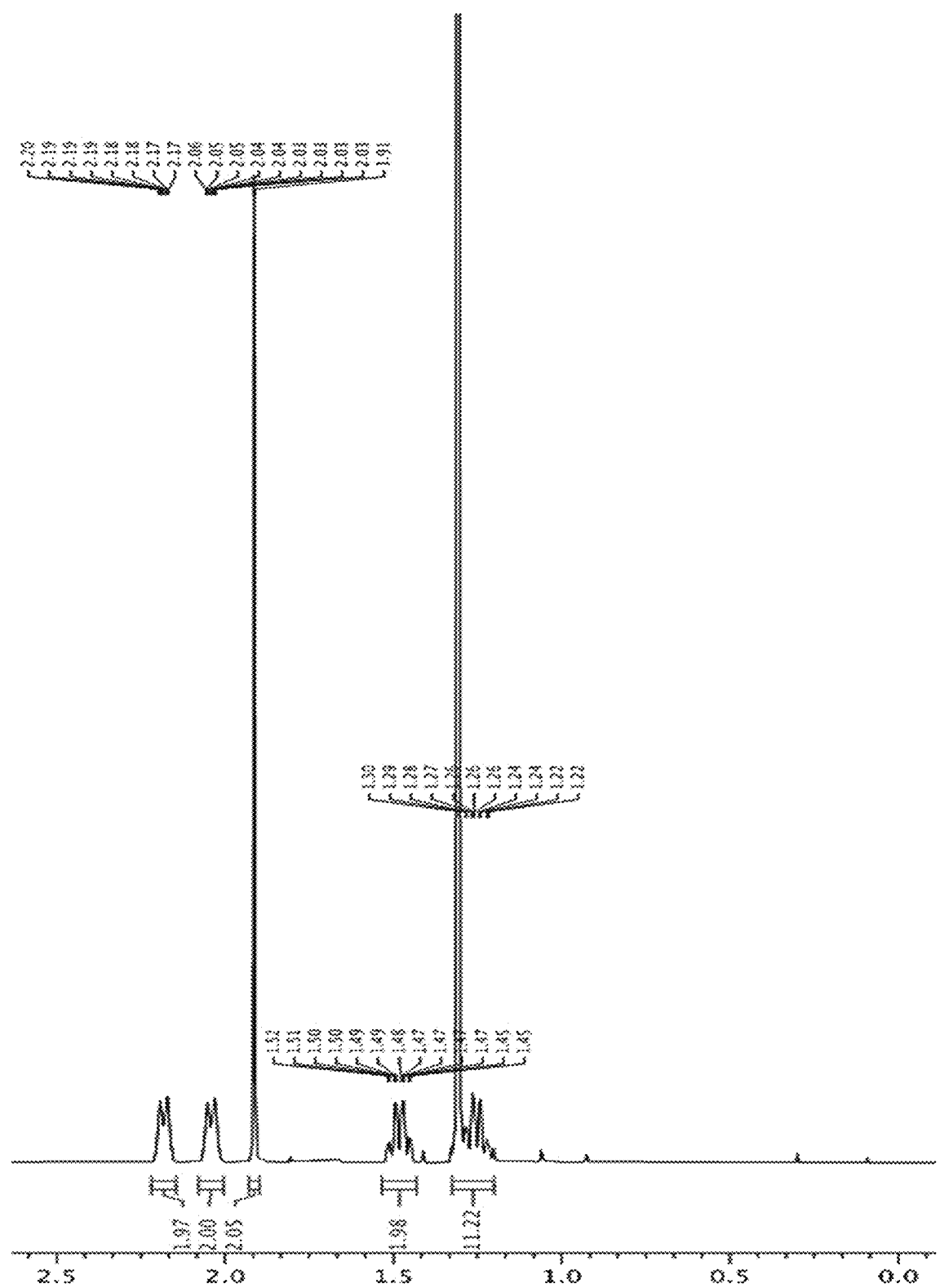
FIG. 6B .cont.

DEVELOPMENT OF A COFILIN INHIBITOR FOR THE TREATMENT OF HEMORRHAGIC BRAIN INJURY-INDUCED NEUROINFLAMMATION

RELATED APPLICATIONS

This application claims priority to U.S. Provisional Application No. 62/851,351 filed under 35 U.S.C. § 111(b) on May 22, 2019, the disclosure of which is incorporated herein by reference in its entirety.

STATEMENT REGARDING FEDERALLY SPONSORED RESEARCH

This invention was made with no government support. The government has no rights in this invention.

BACKGROUND

Every year, an estimated 7 million people suffer from stroke. Intracerebral hemorrhage (ICH), or hemorrhagic stroke, constitutes only about 10-15% of total stroke types, but is responsible for higher mortality rates, and suvivors of hemorrhagic stroke may suffer from severe disabilities and post-stroke cognitive impairments. There is currently no effective therapy available, and identifying signaling molecules with the potential of becoming drug targets after ICH is a difficult undertaking. Thus, there is a need in the art for new treatments for hemorrhagic stroke.

SUMMARY

Provided is a compound comprising Formula I:

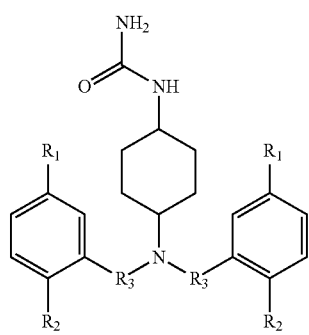

Formula I where each $R_1$ is independently H or a hydrophobic group; each $R_2$ is independently H, a hydrophilic group, or a protecting group; and each $R_3$ is independently $(CH_2)_n$, where n is an integer from 1 to 10. Also provided are racemates, hydrates, solvates, stereoisomers, polymorphs, and prodrugs of Formula I.

In certain embodiments, each $R_1$ is independently selected from the group consisting of H and tert-butyl. In certain embodiments, each $R_2$ is independently selected from the group consisting of H and OH. In certain embodiments, each $R_1$ is independently selected from the group consisting of H and tert-butyl, and each $R_2$ is independently selected from the group consisting of H and OH. In certain embodiments, at least one $R_2$ comprises a tert-butyldimethyl silyl protecting group. In certain embodiments, each $R_3$ is independently selected from the group consisting of $-CH_2-$, $-CH_2CH_2-$, and $-CH_2CH_2CH_2-$.

In certain embodiments, the compound comprises SZ-3:

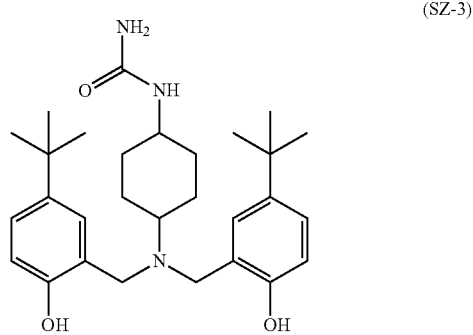 [SMILES: CC(C)(C)c1ccc(O)c(CN(Cc2cc(C(C)(C)C)ccc2O)C2CCC(NC(N)=O)CC2)c1]

(SZ-3)

In particular embodiments, the compound is a prodrug of SZ-3.

In certain embodiments, the compound comprises SZ-2:

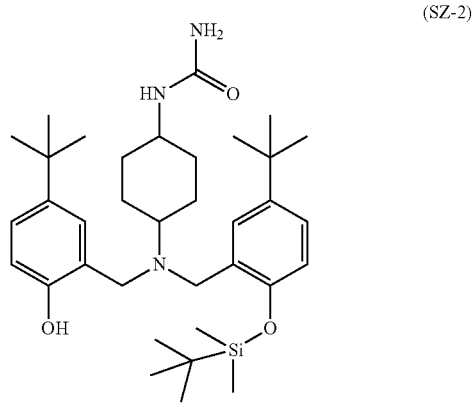 [SMILES: CC(C)(C)c1ccc(O)c(CN(Cc2cc(C(C)(C)C)ccc2O[Si](C)(C)C(C)(C)C)C2CCC(NC(N)=O)CC2)c1]

(SZ-2)

Further provided is a composition comprising a compound of Formula I and a pharmaceutically acceptable carrier, diluent, or adjuvant.

Further provided is a method of inhibiting cofilin activity or reducing total cofilin, the method comprising administering an effective amount of a small molecule to a subject and inhibiting cofilin activity or reducing total cofilin in the subject. In certain embodiments, the small molecule comprises Formula I:

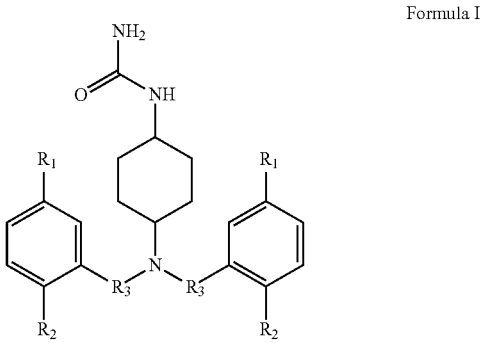

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the small molecule comprises SZ-3:

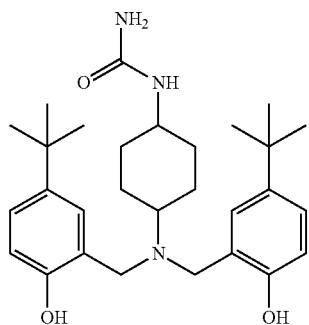

(SZ-3)

In certain embodiments, the small molecule comprises SZ-2:

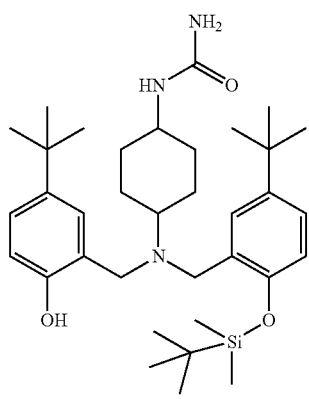

(SZ-2)

Further provided is a method of attenuating LPS-induced microglial activation and inflammation, the method comprising administering an effective amount of a compound to a subject and attenuating LPS-induced microglial activation and inflammation in the subject, wherein the compound comprises Formula I:

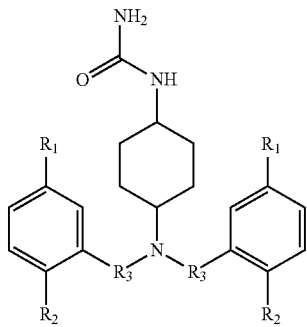

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

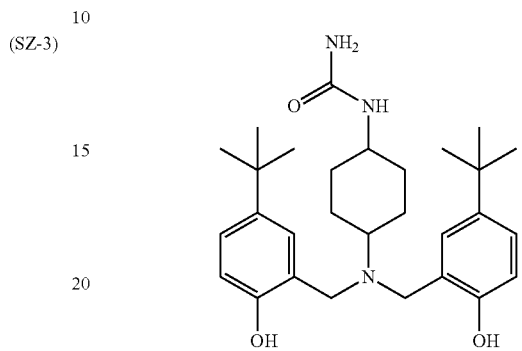

(SZ-3)

In certain embodiments, the compound comprises SZ-2:

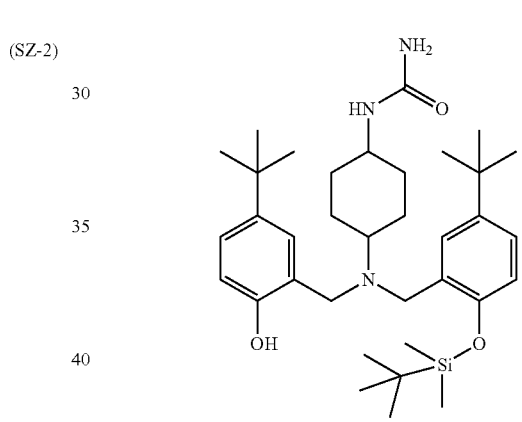

(SZ-2)

Further provided is a method of reducing microglial migration and proliferation, the method comprising administering an effective amount of a compound to a subject and reducing microglial migration and proliferation in the subject, wherein the compound comprises Formula I:

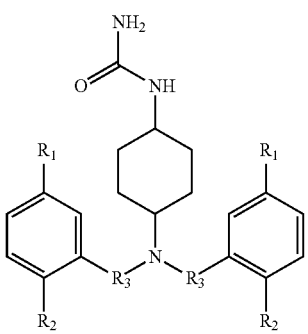

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

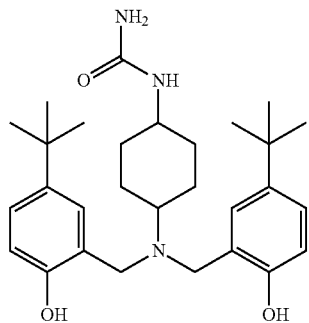

(SZ-3)

In certain embodiments, the compound comprises SZ-2:

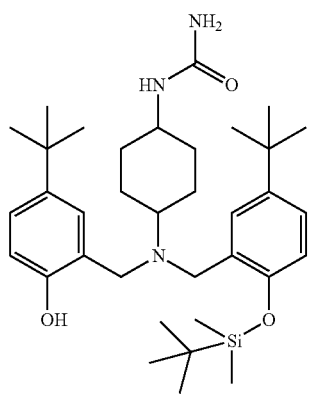

(SZ-2)

Further provided is a method of improving motor deficits in a subject, the method comprising administering an effective amount of a compound to a subject with hemorrhage and improving motor deficits in the subject, wherein the compound comprises Formula I:

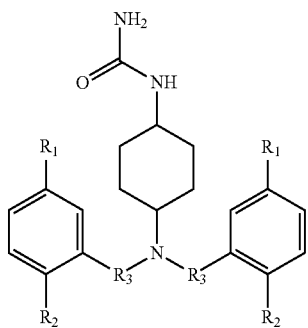

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

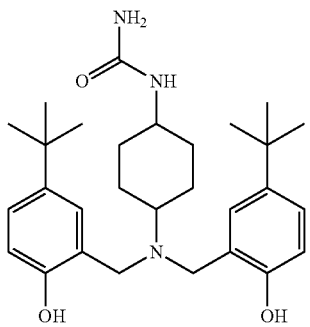

(SZ-3)

In certain embodiments, the compound comprises SZ-2:

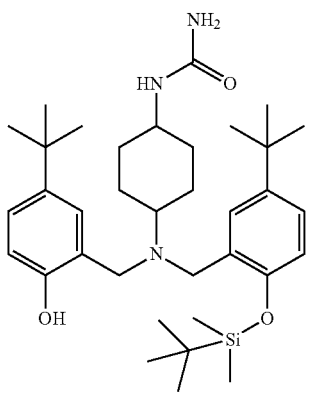

(SZ-2)

Further provided is a method of reducing TNF-α in microglial cells, the method comprising contacting microglial cells with an effective amount of a compound, and reducing TNF-α in the microglial cells, where the compound comprises Formula I:

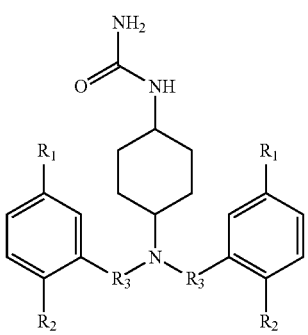

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

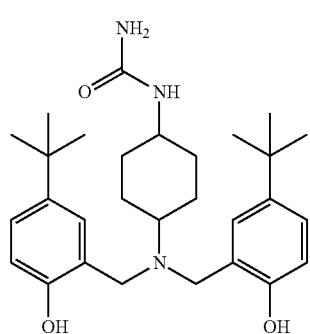

(SZ-3)

In certain embodiments, the compound comprises SZ-2:

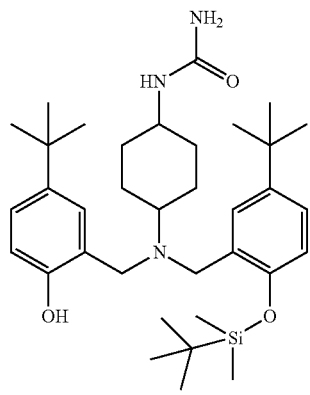

(SZ-2)

Further provided is a method of reducing NF-κB in microglial cells, the method comprising contacting microglial cells with an effective amount of a compound and reducing NF-κB in the microglial cells, wherein the compound comprises Formula I:

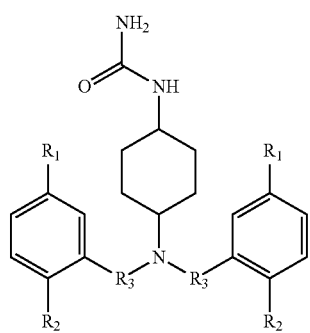

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

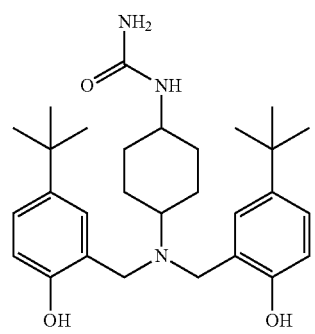

(SZ-3)

In certain embodiments, the compound comprises SZ-2:

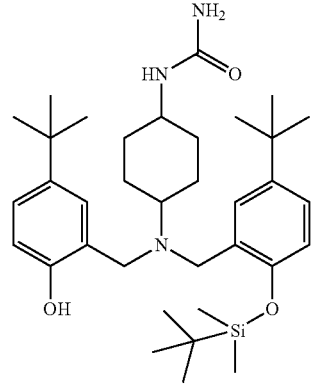

(SZ-2)

Further provided is a method of treating hemorrhagic brain injury-induced neuroinflammation, the method comprising administering to a subject having a hemorrhagic brain injury an effective amount of a compound, and treating hemorrhagic brain injury-induced neuroinflammation in the subject, wherein the compound comprises Formula I:

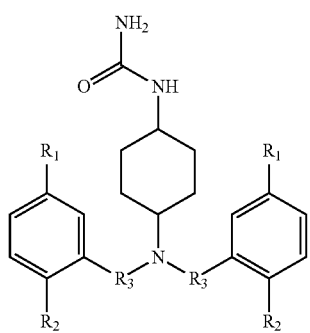

Formula I wherein each $R_1$ is independently H or a hydrophobic group; each $R_2$ is independently H, a hydrophilic group, or a protecting group; and each $R_3$ is independently $(CH_2)_n$, where n is an integer between 1 and 10; or a racemate, hydrate, solvate, stereoisomer, polymorph, or prodrug thereof.

In certain embodiments, the compound comprises SZ-3:

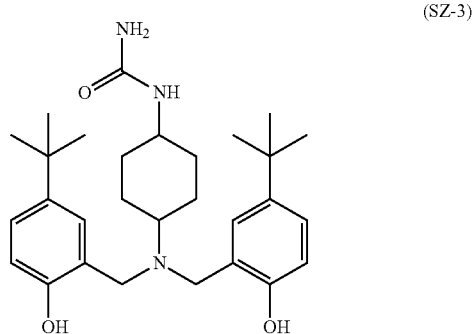 [SMILES: CC(C)(C)c1ccc(O)c(CN(Cc2cc(C(C)(C)C)ccc2O)C2CCC(NC(N)=O)CC2)c1]

(SZ-3)

In certain embodiments, the compound comprises SZ-2:

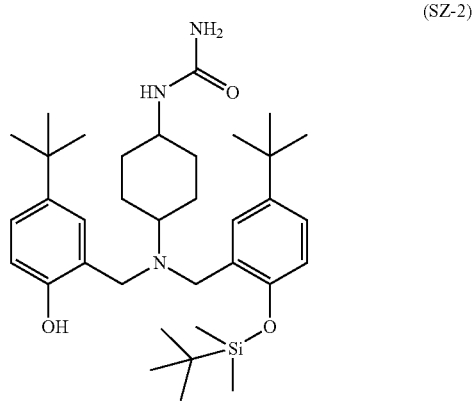 [SMILES: CC(C)(C)c1ccc(O)c(CN(Cc2cc(C(C)(C)C)ccc2O[Si](C)(C)C(C)(C)C)C2CCC(NC(N)=O)CC2)c1]

(SZ-2)

Further provided is the use of a small molecule cofilin inhibitor to treat hemorrhagic brain injury-induced neuroinflammation.

Further provided is the use of a small molecule to inhibit cofilin activity.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8A shows cultured SHSY cells treated with different concentrations of SZ-3. No toxicity was observed in 5-20 μM range. FIG. 8B shows cultured SHSY cells exposed to thrombin 100 U/ml and treated with SZ-3 (20, 10, 5 μM) after 3 h and cells harvested for MTT assay and WB after 24 h. The three concentrations of SZ-3 significantly restored cell death induced by thrombin. FIG. 8C shows WB analysis showing that cofilin expression was increased with thrombin exposure which was reduced by treatment with 5 μM of SZ-3. As cofilin is the target here, its expression in thrombin-challenged SHSY cells was analyzed by WB analysis, and it was observed that SZ-3 treatment significantly reduced cofilin expression (FIG. 8C-FIG. 8D). *p<0.01, ***p<0.0001 relative to thrombin group. These results are from 3 independent experiments using different cell cultures.

FIG. 12A depicts a timeline of the experiment, and photographs of the mice. Control mice (having induced hemorrhage without treatment) suffered from grip strength impairment after 24 h of hemorrhage and mice treated with SZ-3 showed enhanced grip strength (FIG. 12B).

DETAILED DESCRIPTION

Figure 1:
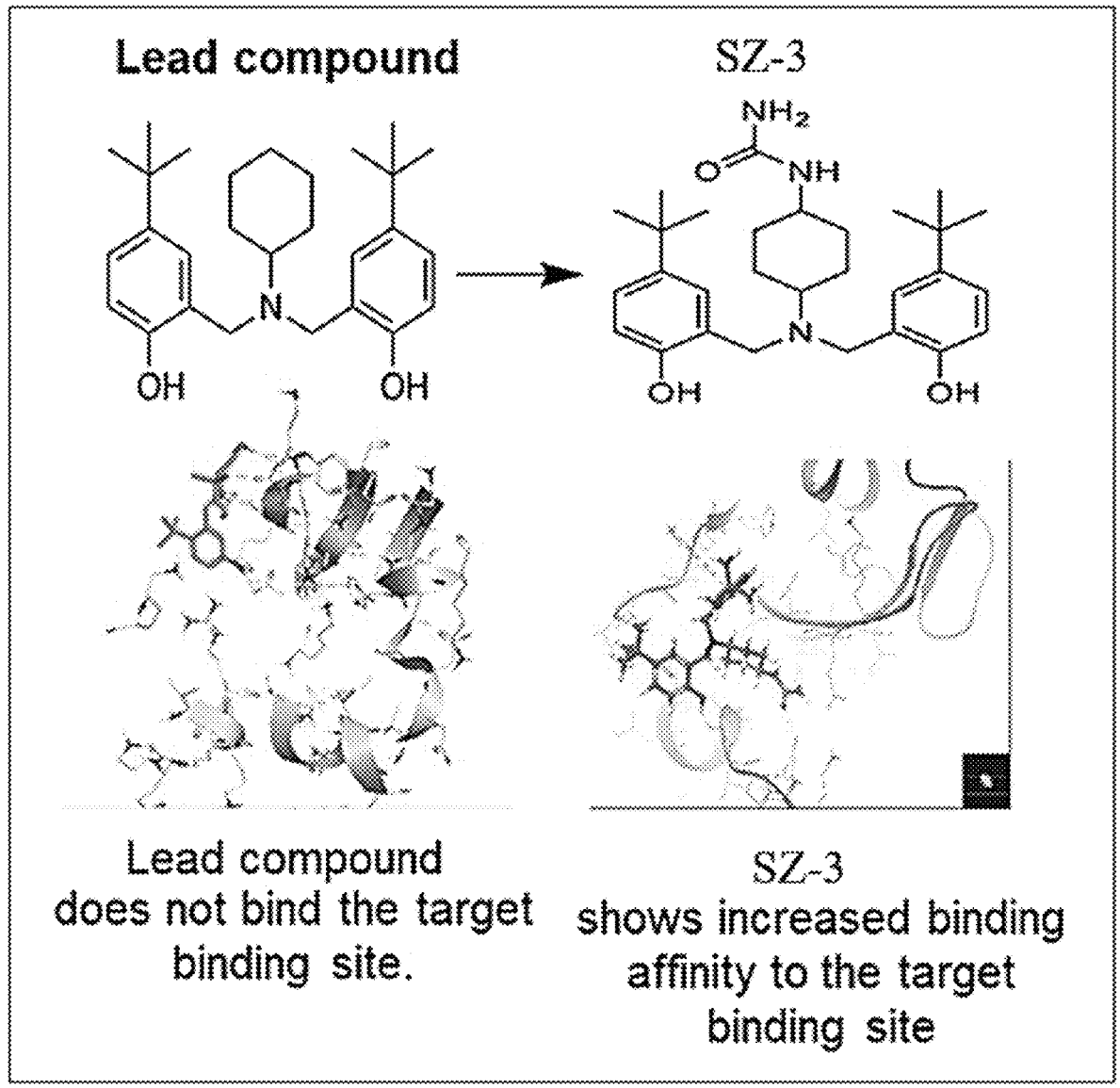
FIG. 1: Protein-ligand binding of the lead-like compound (C-1) and the modified compound (SZ-3). SZ-3 shows increased binding affinity.

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The vast array of cytoskeletal proteins that are involved in neurite outgrowth and neuritogenesis are important mediators of cell death, inflammation, and blood brain barrier (BBB) dysfunction, and may provide useful targets for stroke therapeutics. Cofilin regulates the dynamics of actin filament assembly, disassembly, and organization in most cells, including immune cells of the central nervous system. More importantly, cofilin mediates actin dynamics during macrophage, T-cell, and dendritic activation and migration important for immune reactions. Overactivation of cofilin may lead to microglia inflammation in the brain.

Cofilin siRNA mediated gene knockdown and LPS/heme-treated microglia has shown reduced migration and decreased levels of NO, iNOS, COX2, and TNF-α via NF-κB and JAK-STAT pathway. Similarly, inhibiting cofilin activation with siRNA gene knockdown in mice brains has led to the decreased hematoma volume and improved behavioral outcome with fewer activated microglia and astrocytes following experimental ICH, indicating its important role in mediating inflammatory response. Cofilin inhibition may provide a better motor and functional recovery following hemorrhagic stroke. Current cofilin inhibition tactics include the use of gene deletion, which has many drawbacks such as high cost value, and risk of immune reactions and other off target effects. Therefore, there is a need to develop a small molecule cofilin inhibitor which can inhibit cofilin overactivation mediated microglial activation and neuroinflammation. Provided herein are cofilin inhibitor compounds, their synthesis, and examples of their anti-inflammatory efficacy using in vitro models of human microglial and neuronal cell lines, and in animal models of experimental hemorrhagic stroke.

The cofilin inhibitor compounds in accordance with the present disclosure may have the general structural formula of Formula I:

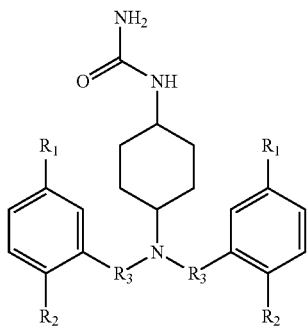

Formula I where each $R_1$ is independently H or a hydrophobic group; each $R_2$ is independently H, a hydrophilic group, or a protecting group; and each $R_3$ is independently $(CH_2)_n$, where n is an integer ranging from 1 to 10. In some embodiments, each $R_1$ is independently selected from the group consisting of H and tert-butyl. In some embodiments, each $R_2$ is independently selected from the group consisting of H and OH. In some embodiments, at least one $R_2$ comprises a tert-butyldimethyl silyl protecting group. In some embodiments, each $R_3$ is independently selected from the group consisting of —$CH_2$—, —$CH_2CH_2$—, and —$CH_2CH_2CH_2$—.

In one non-limiting example, the cofilin inhibitor compound is the compound referred to herein as SZ-3, which has the following structure:

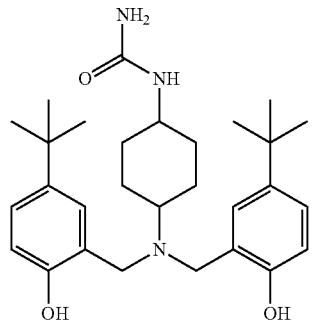

(SZ-3)

SZ-3 is also known as 4-{bis[(5-tert-butyl-2-hydroxyphenyl)methyl]amino}cyclohexyl urea. SZ-3 can be prepared, by way of a non-limiting example, through the synthesis depicted in Schemes 1-2 shown in FIGS. 2-3 and further described in the examples herein.

Figure 2:
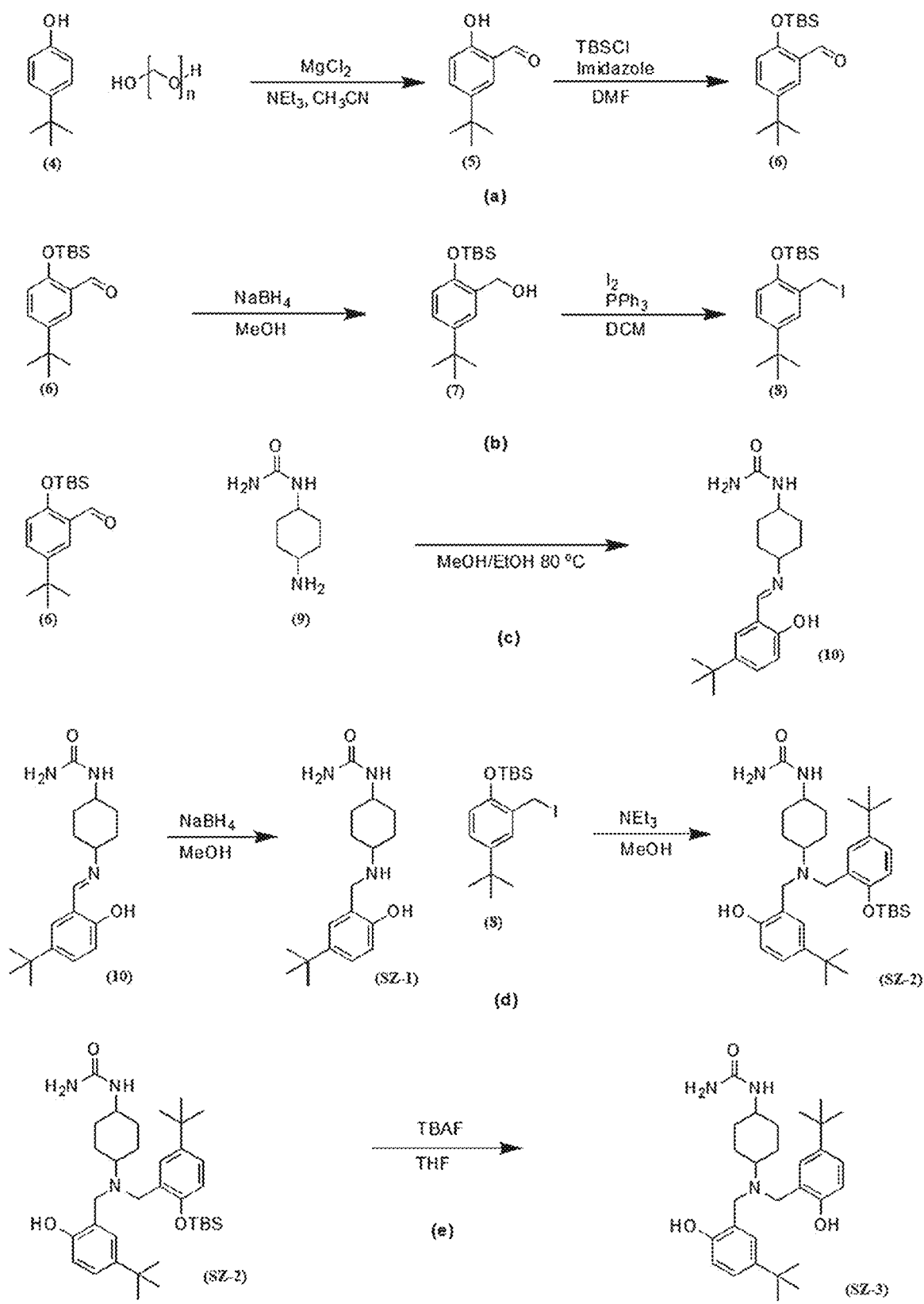
FIG. 2: Scheme 1, showing a non-limiting example synthesis for SZ-3.
Figure 3:
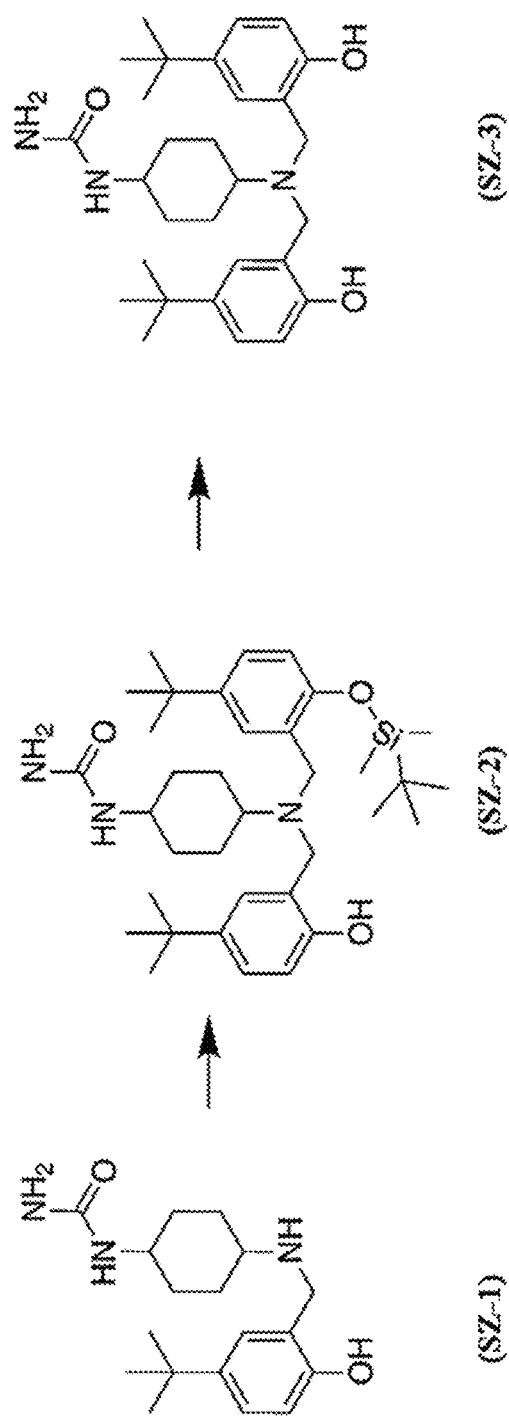
FIG. 3: Scheme 2, showing a summary of steps (d) and (e) in Scheme 1 depicted in FIG. 2 for the synthesis of SZ-3.

As seen in FIGS. 2-3, the synthesis of SZ-3 may involve the use of one or more protecting groups. However, when one side of the Formula I structure is still protected, the compound still works to inhibit cofilin. Thus, in some embodiments, the cofilin inhibitor compound is the compound referred to herein as SZ-2, which has the following structure:

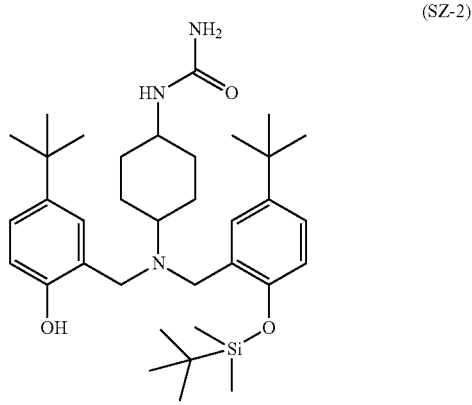 [SMILES: CC(C)(C)c1ccc(O)c(CN(Cc2cc(C(C)(C)C)ccc2O[Si](C)(C)C(C)(C)C)C2CCC(NC(N)=O)CC2)c1]

(SZ-2)

As seen above, compared to SZ-3, SZ-2 includes a tert-butyldimethyl silyl ("TBS") protecting group in place of the hydroxyl on one of the phenyl rings, to create a tert-butyldimethyl silyl ether ("OTBS"). SZ-2 can be prepared, by way of a non-limiting example, through the synthesis depicted in Schemes 1-2 shown in FIGS. 2-3 and further described in the examples herein, where SZ-2 is synthesized and isolated as part of the process for preparing SZ-3.

The cofilin inhibitor compounds herein may be useful to effectively target cofilin, particularly during secondary injury following ICH. The cofilin inhibitor compounds may also be useful in neurodegenerative disease and aging, and may be useful in improving motor deficits. Furthermore, the cofilin inhibitor compounds may be useful for treating other diseases, or producing other effects, correlated with cofilin. For example, the cofilin inhibitor compounds may be useful for treating glioblastoma.

Pharmaceutical compositions of the present disclosure comprise an effective amount of a compound of Formula I (such as, but not limited to, SZ-3 or SZ-2), or salt, racemate, hydrate, solvate, polymorph, or prodrug thereof (an "active ingredient"), and/or additional agents, dissolved or dispersed in a pharmaceutically acceptable carrier. The phrases "pharmaceutical" or "pharmacologically acceptable" refer to molecular entities and compositions that produce no adverse, allergic, or other untoward reaction when administered to an animal, such as, for example, a human. The preparation of a pharmaceutical composition that contains at least one compound or additional active ingredient will be known to those of skill in the art in light of the present disclosure, as exemplified by Remington's Pharmaceutical Sciences, 2003, incorporated herein by reference. Moreover, for animal (e.g., human) administration, it is understood that preparations should meet sterility, pyrogenicity, general safety, and purity standards as required by FDA Office of Biological Standards.

A composition disclosed herein may comprise different types of carriers depending on whether it is to be administered in solid, liquid or aerosol form, and whether it need to be sterile for such routes of administration as injection. Compositions disclosed herein can be administered intravenously, intradermally, transdermally, intrathecally, intraarterially, intraperitoneally, intranasally, intravaginally, intrarectally, intraosseously, periprosthetically, topically, intramuscularly, subcutaneously, mucosally, intraosseosly, periprosthetically, in utero, orally, topically, locally, via inhalation (e.g., aerosol inhalation), by injection, by infusion, by continuous infusion, by localized perfusion bathing target cells directly, via a catheter, via a lavage, in cremes, in lipid compositions (e.g., liposomes), or by other method or any combination of the forgoing as would be known to one of ordinary skill in the art (see, for example, Remington's Pharmaceutical Sciences, 2003, incorporated herein by reference).

The actual dosage amount of a composition disclosed herein administered to an animal or human patient can be determined by physical and physiological factors such as body weight, severity of condition, the type of disease being treated, previous or concurrent therapeutic interventions, idiopathy of the patient, and on the route of administration. Depending upon the dosage and the route of administration, the number of administrations of a preferred dosage and/or an effective amount may vary according to the response of the subject. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a composition herein and/or additional agent is formulated to be administered via an alimentary route. Alimentary routes include all possible routes of administration in which the composition is in direct contact with the alimentary tract. Specifically, the pharmaceutical compositions disclosed herein may be administered orally, buccally, rectally, or sublingually. As such, these compositions may be formulated with an inert diluent or with an assimilable edible carrier, or they may be enclosed in hard- or soft-shell gelatin capsules, they may be compressed into tablets, or they may be incorporated directly with the food of the diet.

In further embodiments, a composition described herein may be administered via a parenteral route. As used herein, the term "parenteral" includes routes that bypass the alimentary tract. Specifically, the pharmaceutical compositions disclosed herein may be administered, for example but not limited to, intravenously, intradermally, intramuscularly, intraarterially, intrathecally, subcutaneous, or intraperitoneally (U.S. Pat. Nos. 6,753,514, 6,613,308, 5,466,468, 5,543,158, 5,641,515, and 5,399,363 are each specifically incorporated herein by reference in their entirety).

Solutions of the compositions disclosed herein as free bases or pharmacologically acceptable salts may be prepared in water suitably mixed with a surfactant, such as hydroxypropylcellulose. Dispersions may also be prepared in glycerol, liquid polyethylene glycols and mixtures thereof, and in oils. Under ordinary conditions of storage and use, these preparations may contain a preservative to prevent the growth of microorganisms. The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In some cases, the form should be sterile and should be fluid to the extent that easy injectability exists. It should be stable under the conditions of manufacture and storage and should be preserved against the contaminating action of microorganisms, such as bacteria and fungi. The carrier can be a solvent or dispersion medium containing, for example, water, ethanol, polyol (i.e., glycerol, propylene glycol, liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and antifungal agents, such as, but not limited to, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption such as, for example, aluminum monostearate or gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that can be employed will be known to those of skill in the art in light of the present disclosure. For example, one dosage may be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

Sterile injectable solutions are prepared by incorporating the compositions in the required amount in the appropriate solvent with various other ingredients enumerated above, as required, followed by filtered sterilization. Generally, dispersions are prepared by incorporating the various sterilized compositions into a sterile vehicle which contains the basic dispersion medium and the required other ingredients from those enumerated above. In the case of sterile powders for the preparation of sterile injectable solutions, some methods of preparation are vacuum-drying and freeze-drying techniques which yield a powder of the active ingredient plus any additional desired ingredient from a previously sterile-filtered solution thereof. A powdered composition is combined with a liquid carrier such as, but not limited to, water or a saline solution, with or without a stabilizing agent.

In other embodiments, the compositions may be formulated for administration via various miscellaneous routes, for example, topical (i.e., transdermal) administration, mucosal administration (intranasal, vaginal, etc.), and/or via inhalation.

Pharmaceutical compositions for topical administration may include the compositions formulated for a medicated application such as an ointment, paste, cream, or powder. Ointments include all oleaginous, adsorption, emulsion, and water-soluble based compositions for topical application, while creams and lotions are those compositions that include an emulsion base only. Topically administered medications may contain a penetration enhancer to facilitate adsorption of the active ingredients through the skin. Suitable penetration enhancers include glycerin, alcohols, alkyl methyl sulfoxides, pyrrolidones, and luarocapram. Possible bases for compositions for topical application include polyethylene glycol, lanolin, cold cream, and petrolatum, as well as any other suitable absorption, emulsion, or water-soluble ointment base. Topical preparations may also include emulsifiers, gelling agents, and antimicrobial preservatives as necessary to preserve the composition and provide for a homogenous mixture. Transdermal administration of the compositions may also comprise the use of a "patch." For example, the patch may supply one or more compositions at a predetermined rate and in a continuous manner over a fixed period of time.

In certain embodiments, the compositions may be delivered by eye drops, intranasal sprays, inhalation, and/or other aerosol delivery vehicles. Methods for delivering compositions directly to the lungs via nasal aerosol sprays has been described in U.S. Pat. Nos. 5,756,353 and 5,804,212 (each specifically incorporated herein by reference in their entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts and could be employed to deliver the compositions described herein. Likewise, transmucosal drug delivery in the form of a polytetrafluoroetheylene support matrix is described in U.S. Pat. No. 5,780,045 (specifically incorporated herein by reference in its entirety), and could be employed to deliver the compositions described herein.

It is further envisioned the compositions disclosed herein may be delivered via an aerosol. The term aerosol refers to a colloidal system of finely divided solid or liquid particles dispersed in a liquefied or pressurized gas propellant. The typical aerosol for inhalation consists of a suspension of active ingredients in liquid propellant or a mixture of liquid propellant and a suitable solvent. Suitable propellants include hydrocarbons and hydrocarbon ethers. Suitable containers will vary according to the pressure requirements of the propellant. Administration of the aerosol will vary according to subject's age, weight, and the severity and response of the symptoms.

In particular embodiments, the compounds and compositions described herein are useful for treating hemorrhagic brain injury-induced neuroinflammation, as well as neurodegenerative diseases, and may also be useful for improving motor deficits, attenuating LPS-induced microglial activation and inflammation, reducing microglial migration and proliferation, reducing TNF-α, and reducing NF-78 B. The compounds and compositions may also be useful for treating diseases known to be correlated to cofilin activity, such as glioblastoma. Furthermore, the compounds and compositions herein can be used in combination therapies. That is, the compounds and compositions can be administered concurrently with, prior to, or subsequent to one or more other desired therapeutic or medical procedures or drugs. The particular combination of therapies and procedures in the combination regimen will take into account compatibility of the therapies and/or procedures and the desired therapeutic effect to be achieved. Combination therapies include sequential, simultaneous, and separate administration of the active compound in a way that the therapeutic effects of the first administered procedure or drug is not entirely disappeared when the subsequent procedure or drug is administered.

By way of a non-limiting example of a combination therapy, the compounds or compositions described herein can be administered in combination with one or more suitable antihypertension drugs which may typically be administered to treat a stroke including, but not limited to: thiazide diuretics, calcium channel blockers, ACE inhibitors, angiotensin II receptor antagonists (ARBs), beta blockers, or combinations thereof. As another example of a combination therapy, the compounds or compositions described herein can be administered in combination with a thrombolytic therapy. Suitable thrombolytic drugs include, but are not limited, eminase, retavase, streptase, t-Pa, TNKase, and abbokinase drugs.

EXAMPLES

The "lead compound" depicted in FIG. 1 was obtained from the ZINC database library containing 6,053,287 molecules. The molecules in the library were filtered based on properties such as molecular weight less than 350, and the calculated octanol:water partition coefficient (log P) less than 4, to provide a lead-like molecule suitable for further modification. Molecules with such properties have a better chance of binding to a receptor, because they can more easily find a binding mode than larger molecules. Since cofilin inhibitors have not previously been crystallized, SwissDock, Glide, and MOE docking programs were used to scan the crystal structure of cofilin and characterize the entire surface of the protein for pockets depth (grooves) and hydrophobicity, revealing any potential target binding sites (FIG. 1). One of the highest score pockets that was located close to the area involved in binding to F-actin only (C-terminal) was selected for further docking studies. The software was used to search 3D databases of lead molecules and ranked each candidate on the basis of the best scoring functions using mathematical calculations to predict the strength of binding affinity between ligands and protein. The highest scoring lead molecule was selected, but molecular modeling showed the molecule (referred to in FIG. 1 as the "lead compound") was not binding the target binding site (FIG. 1). Therefore, the molecule modification strategy was focused on increasing the calculated binding affinity by adding a functional group in the para position of aminocyclohexane to anchor the molecule in the deep groove of the potential binding pocket, and maintaining the Gibbs free energy of binding (ΔG) as low as possible by substituting functional groups with bioisosteres (i.e., different groups that have the same physical or chemical properties) (FIG. 1). The modified analogue (SZ-3) was found to bind the potential binding pocket of F-actin.

Example I—Preparation of SZ-3

As seen in FIG. 2, compound SZ-3 was synthesized by reductive amination of aldehydes. The reaction was started with 4-(tert-butyl) phenol (8) and paraformaldehyde to allow formylation of phenols. Separately, the hydroxyl group of 5-tert-butyl-2-hydroxybenzaldehyde (5) was protected with tert-butyldimethylsilyl chloride (TBDMS-Cl), then mixed with (4-aminocyclohexyl)urea (9) in dry methanol to form an imine (10). This product (10) was treated with a mild reducing agent such as triacetoxyborohydride to form a secondary amine (SZ-1). The protected 5-tert-butyl-2-hydroxybenzaldehyde (6) was reduced by sodium borohydride (NaBH$_4$), then the alcohol was substituted by iodine to produce an aryl iodide (8). Finally, tert-butyl({[4-tert-butyl-2-(iodomethyl)phenyl]methyl})dimethylsilane (8), 4-{[(5-tert-butyl-2 hydroxyphenyl)methyl]amino}cyclohexylurea (SZ-1), and trimethylamine were mixed at room temperature under inert atmosphere to yield SZ-2, the compound was deprotected, and the final purification was performed by column chromatography to yield compound SZ-3 (FIG. 2).

Phenol Formylation

As shown in step (a) of Scheme 1 (FIG. 2), dry triethylamine was added to a solution of 4-(tert-butyl) phenol (4), paraformaldehyde, and an-hydrous Mg. The mixture was refluxed for 4 h, then cooled to RT. The mixture was extracted with EtOAc, the organic layer was dried over MgS and filtered, and then purified by column chromatography. 5-tert-butyl-2-hydroxybenzaldehyde (5) was prepared for the next reaction by protection of the hydroxyl group with tert-butyldimethylsilyl chloride (TBDMS-Cl) in DMF with the presence of imidazole. The product was the protected and formylated compound (6):

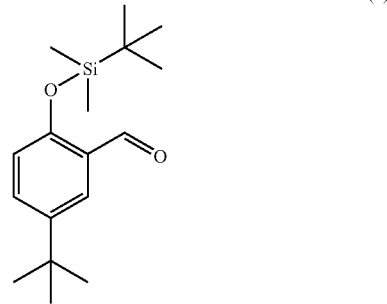

(6)

Synthesis of Aryl Iodide

The reducing agent NaBH$_4$ was added to the protected 5-tert-butyl-2-hydroxybenzaldehyde (6) in anhydrous MeOH to form protected 4-tert-butyl-2-(hydroxymethyl) phenol (7). To a solution of PPh$_3$ in CH$_2$Cl$_2$, resublimed iodine was added and the mixture was stirred at room temperature for 5 min. Then, the protected 4-tert-butyl-2-(hydroxymethyl)phenol (7) was added, and the mixture was further stirred for 2 h. Then, the reaction was extracted with EtOAc. The organic layer was dried over MgSO$_4$, filtered, and then purified by column chromatography. The product was the protected aryl iodide (8):

(8)

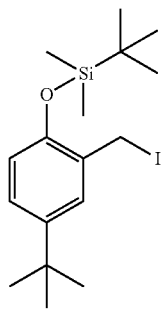

Schiff Bases

Schiff bases were prepared by dissolving 4-aminocyclohexylurea (9), dry methanol, and ethanol at 80° C. The mixture was cooled to around 40° C., and 5-(tert-butyl)-2-((tert-butyldimethylsilyl)oxy)benzaldehyde (6) was added. Notably, the MeOH/EtOH was heated to 80° C. with cyclohexyl/urea to dissolve it, then cooled but not to a low enough temperature to cause precipitation. It is at this point that the other reactant was introduced. Following the addition of tert-butyl-({[4-tert-butyl-2-(iodomethyl)phenyl]methyl})-dimethylsilane (6), the mixture was stirred at 80° C. again. The progress of the reaction was monitored by TLC. On completion of the reaction, the product was separated as a yellow-colored amorphous product which was filtered, dried, and recrystallized from methanol. The product was the Schiff base 4{[(5-tert-butyl-2-hydroxyphenyl)methyl]amino}-cyclohexylurea (10):

(10)

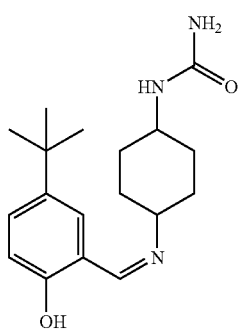

Synthesis of SZ-3 from SZ-1 (FIG. 3)

4{[(5-tert-butyl-2-hydroxyphenyl)methyl]amino}cyclohexylurea (10) was treated with sodium borohydride in anhydrous MeOH under nitrogen to form a secondary amine, 4[(E)[(5-tert-butyl-2-hydroxyphenyl)methylidene]amino]cyclohexylurea (SZ-1). Tert-butyl({[4-tert-butyl-2-(iodomethyl)phenyl]methyl})dimethylsilane (8) was then introduced to the mixture and stirred for 5 min, after which triethylamine was added and stirred overnight. Finally, the purified product (SZ-2) was deprotected by dissolving it in THF. Then, the tetrabutylammonium fluoride trihydrate reaction was added and stirred for 1 h at RT. Compound SZ-3 was extracted with EtOAc. The organic layer was dried over $MgSO_4$, filtered, and purified by column chromatography.

Figure 4A:
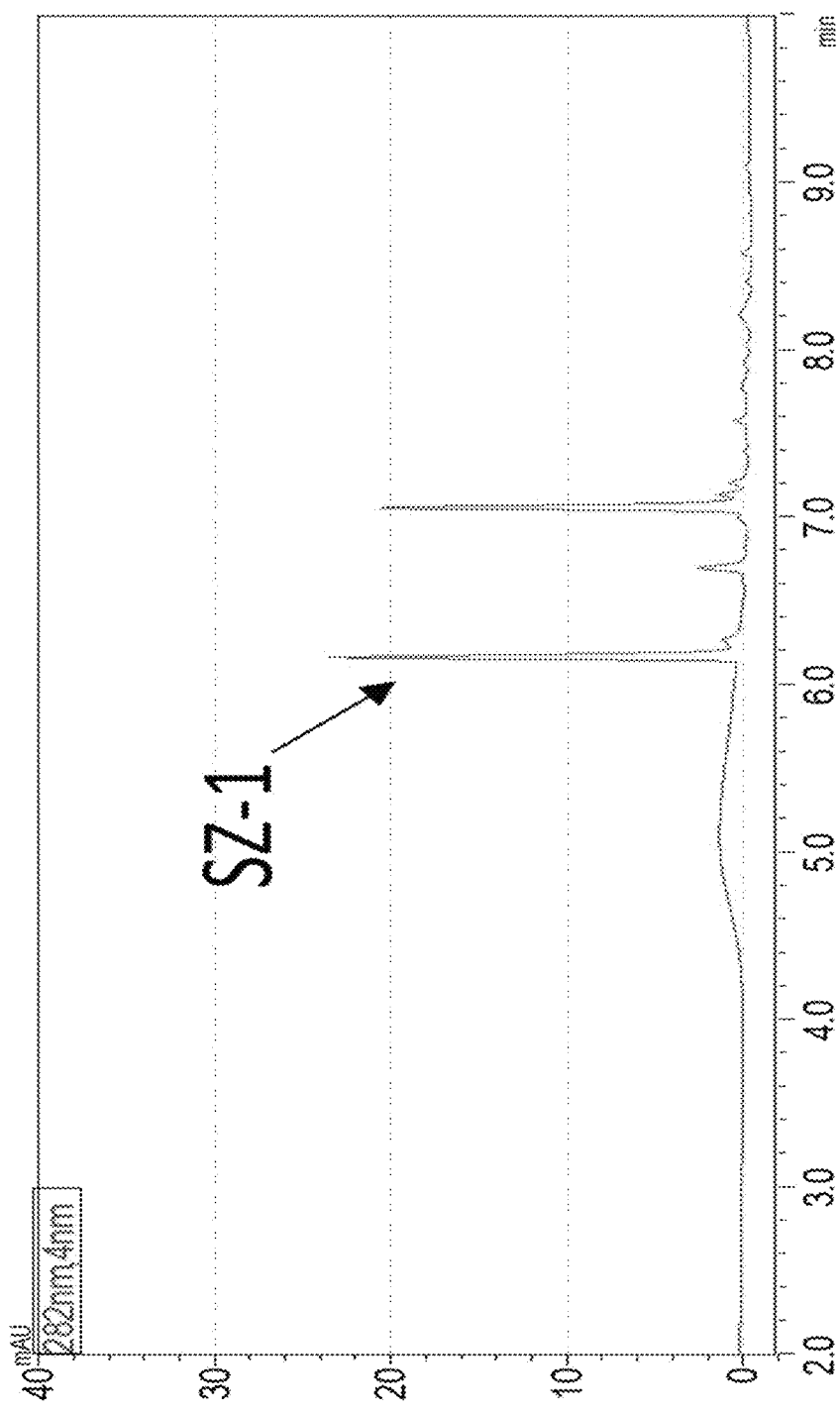
FIGS. 4A-4C: High-performance liquid chromatography (HPLC) chromatograms of SZ-1 (FIG. 4A), SZ-2 (FIG. 4B), and SZ-3 (FIG. 4C).
Figure 4B:
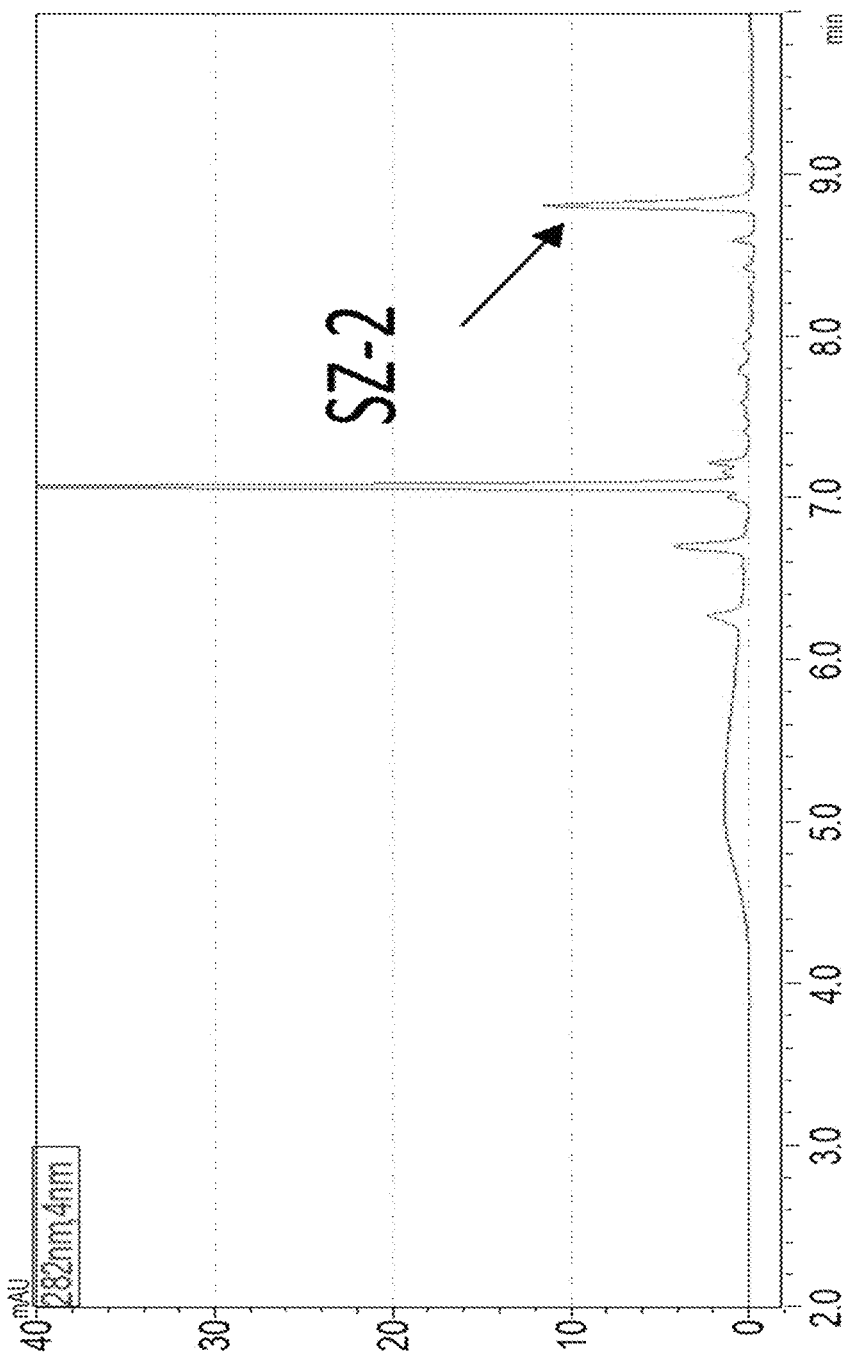
Figure 4B:
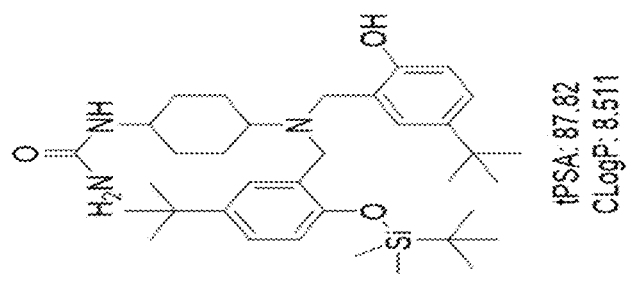
Figure 4C:
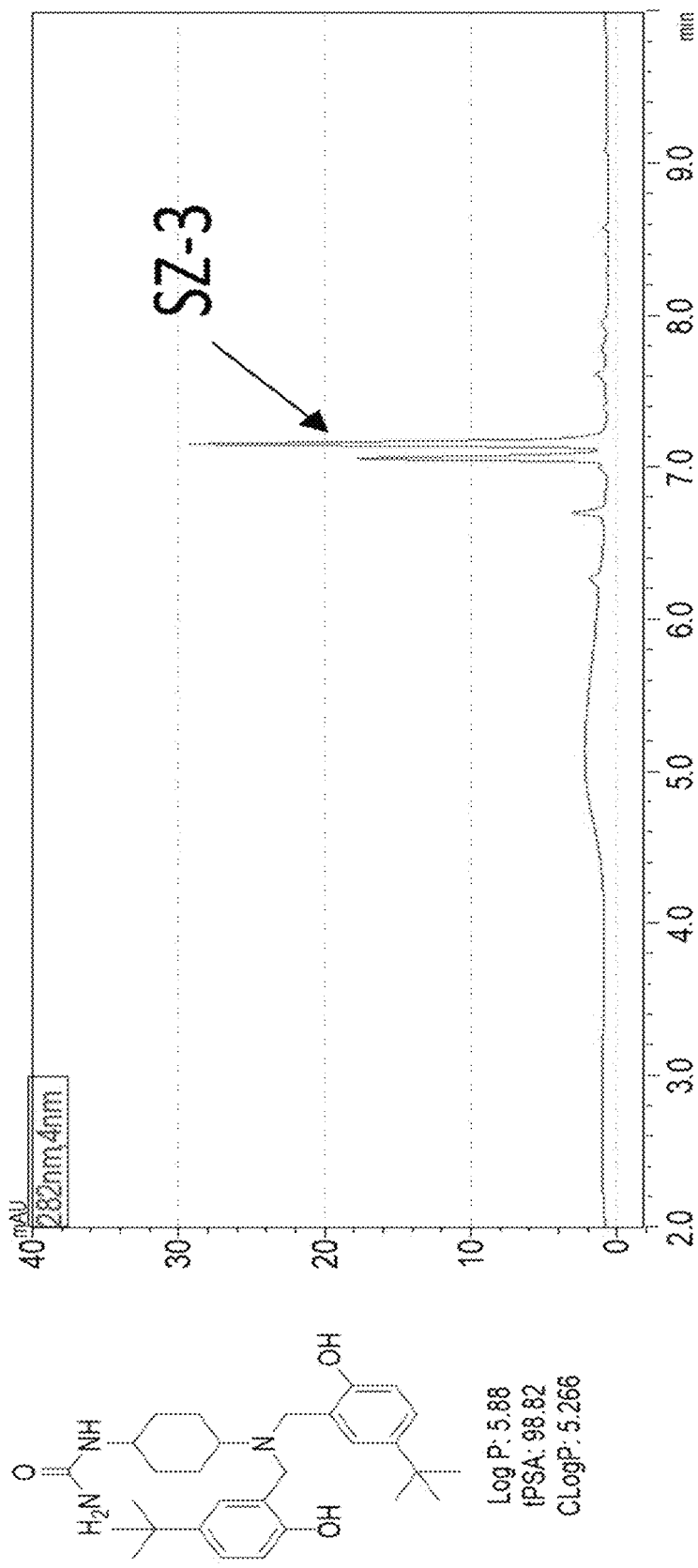
Figure 5:
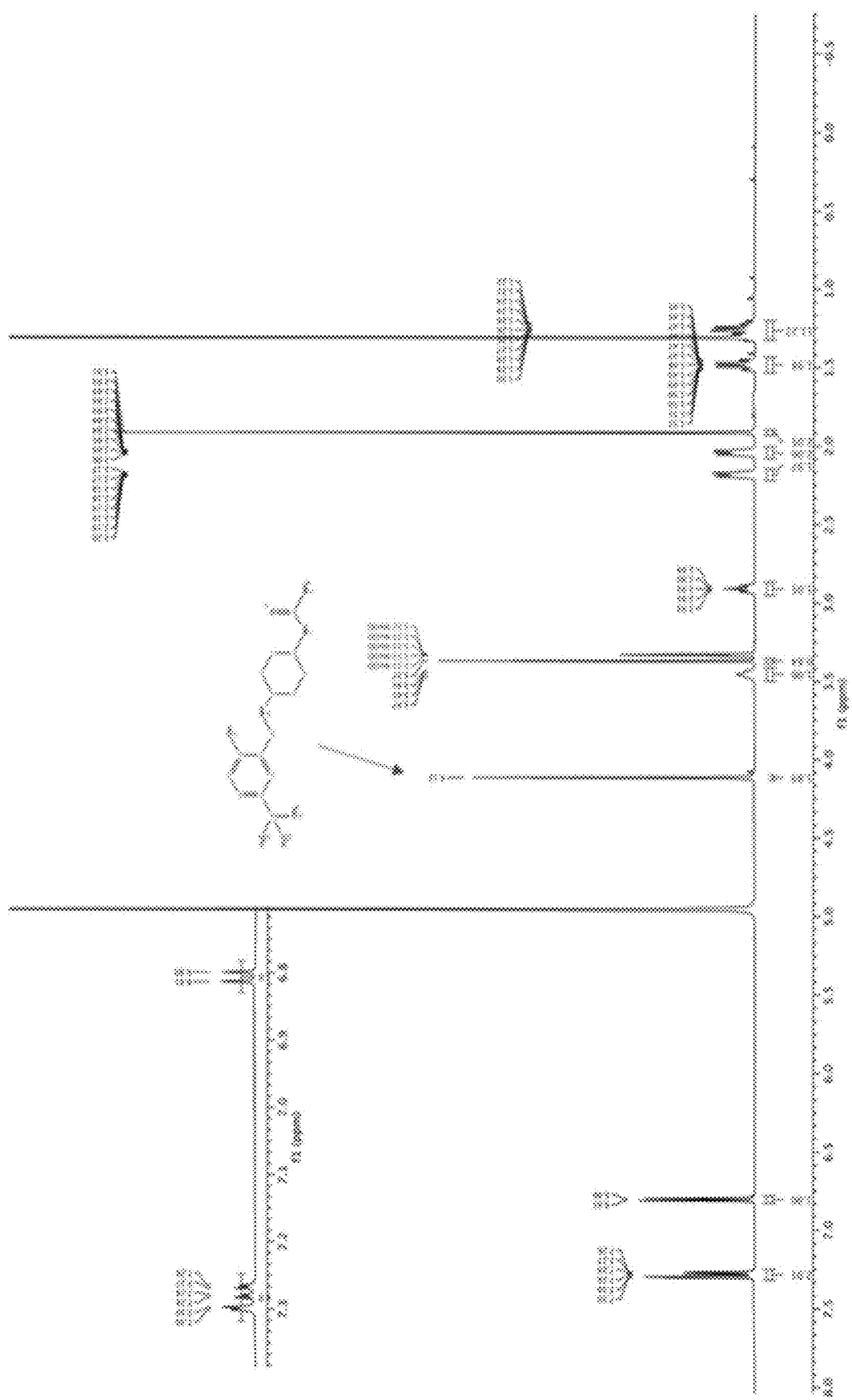
FIG. 5: $^1$H NMR spectrum of the synthesized enamine SZ-1.
Figure 5:
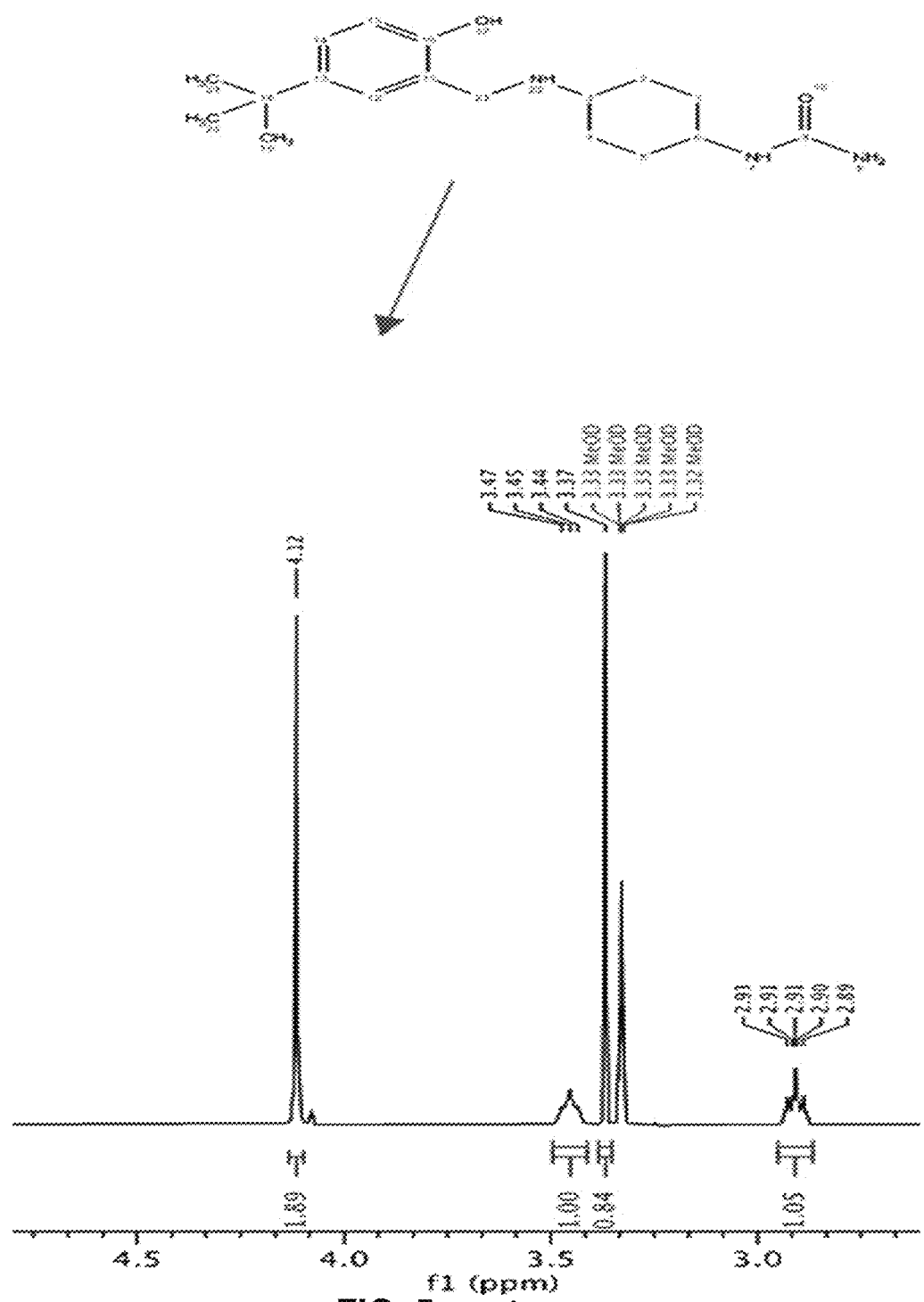
Figure 5:
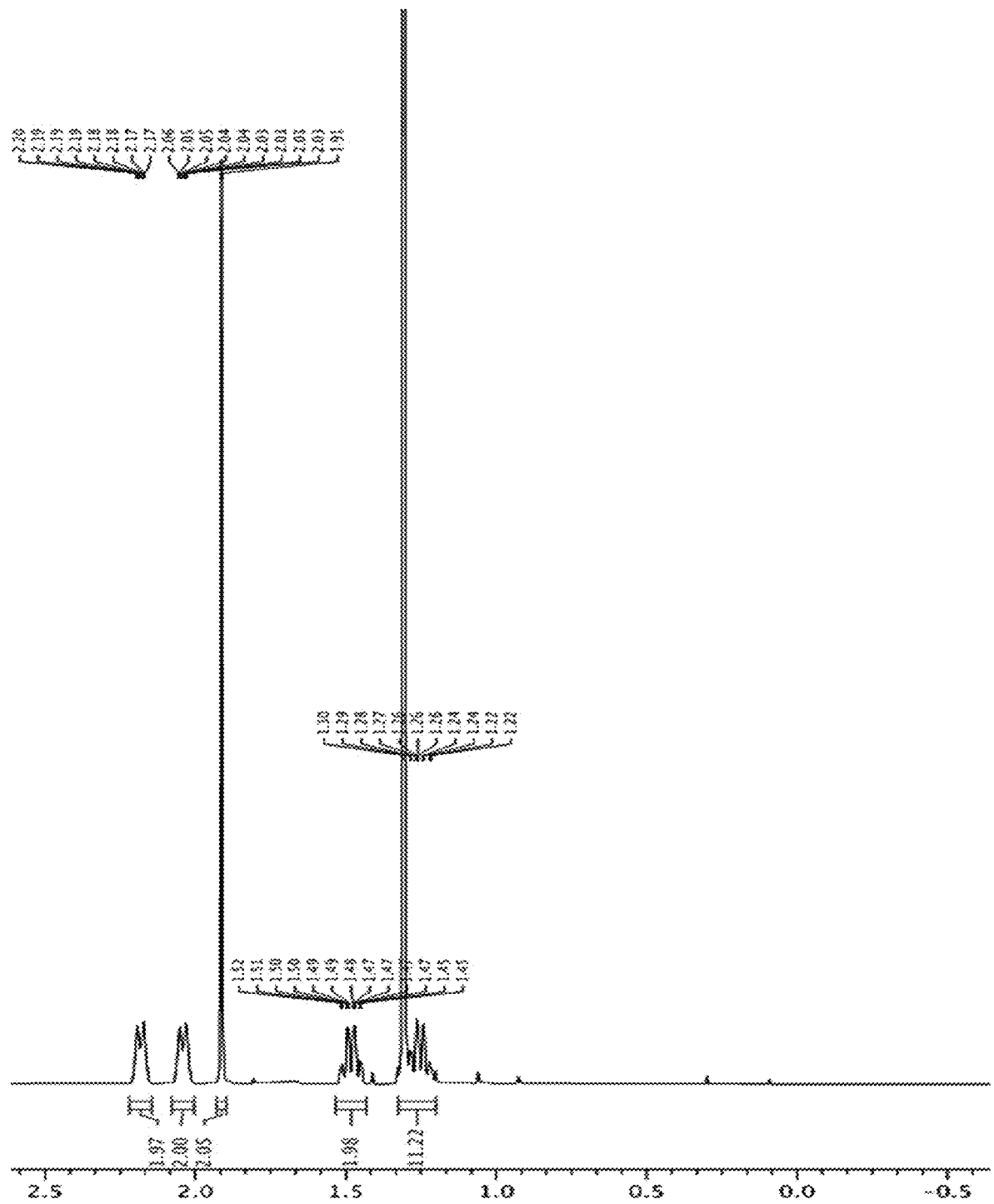
Figure 6A:
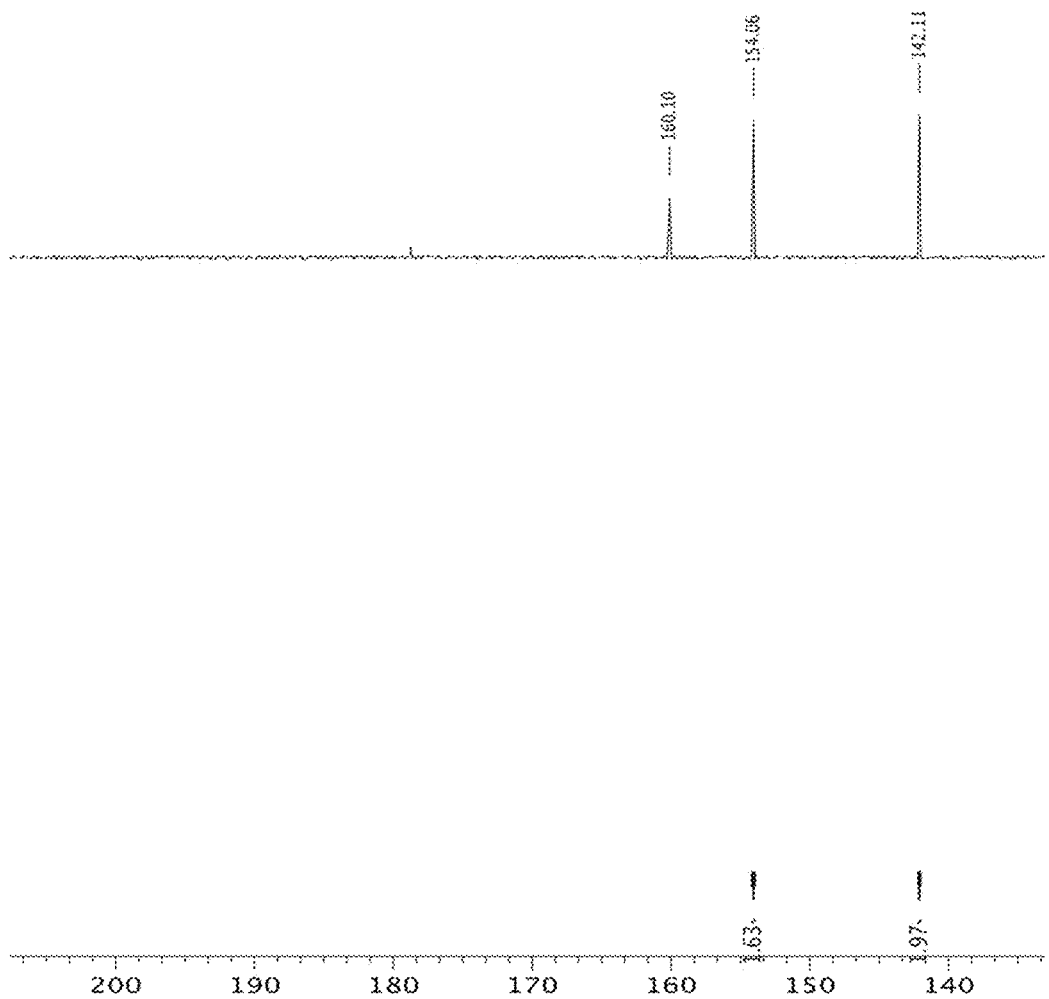
FIGS. 6A-6B: $^{13}$C NMR attached proton test (APT) (FIG. 6A) and $^1$H NMR (FIG. 6B) spectra of the synthesized SZ-3.
Figure 6A:
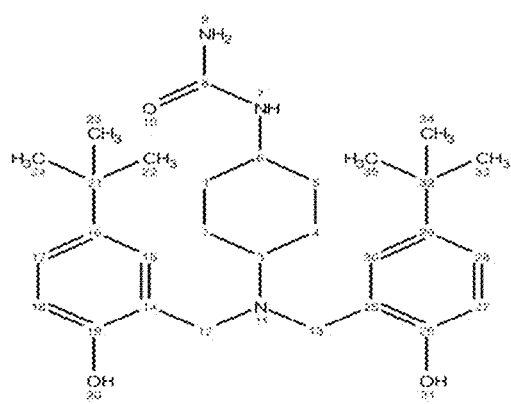
Figure 6A:
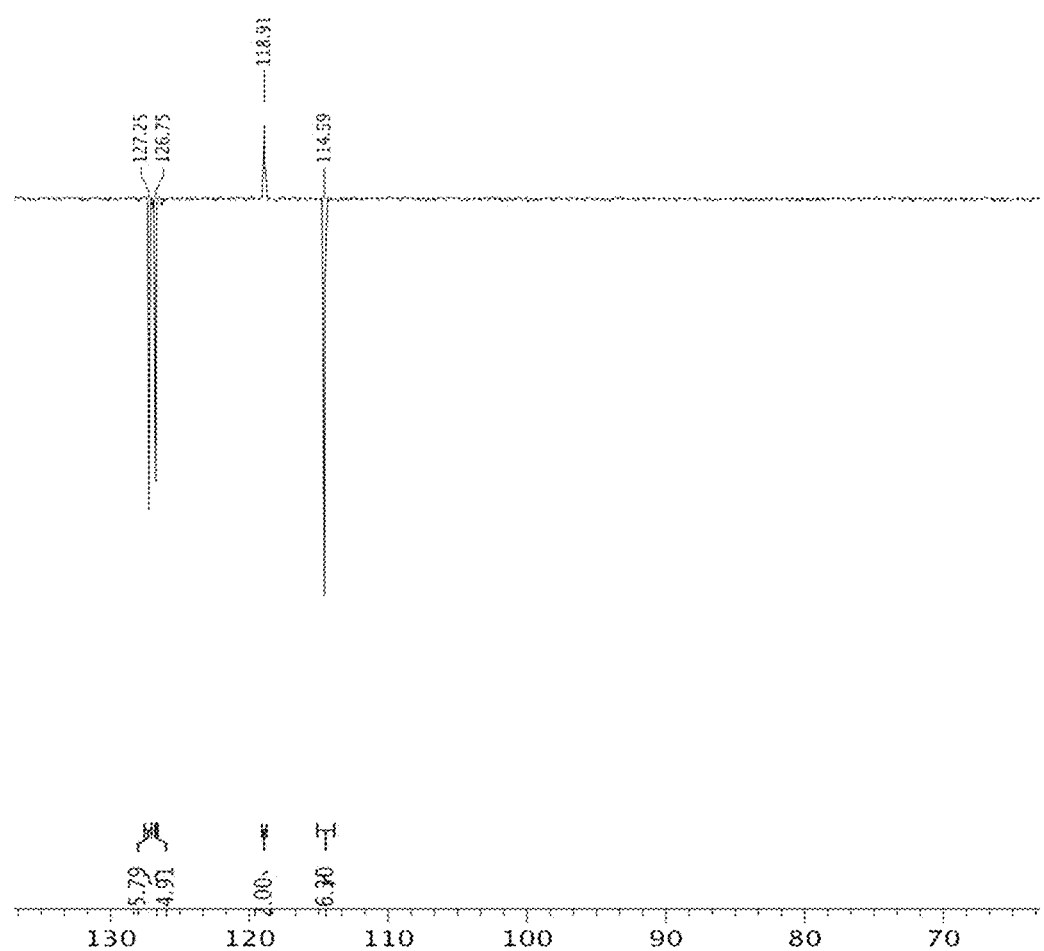
Figure 6A:
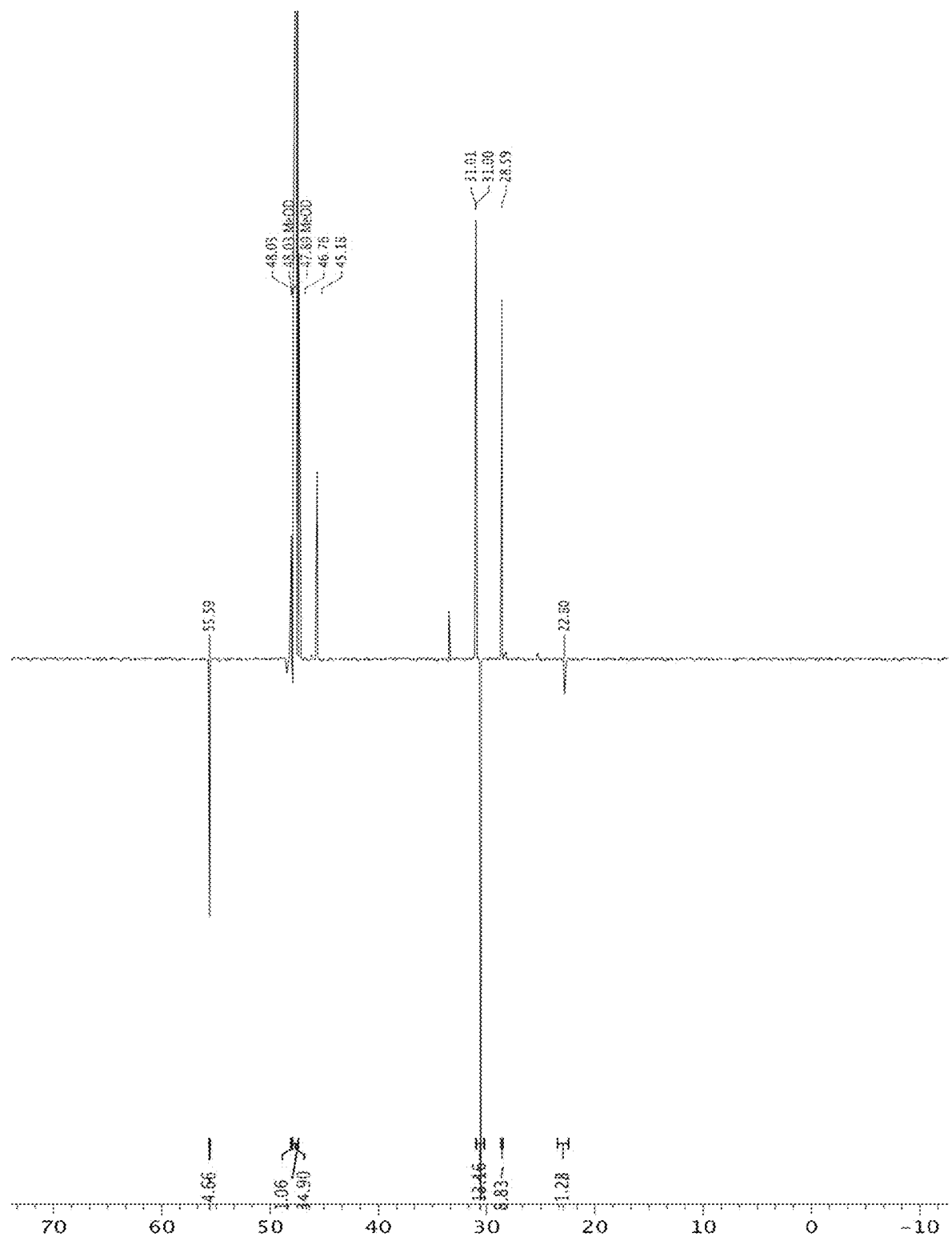
Figure 6B:
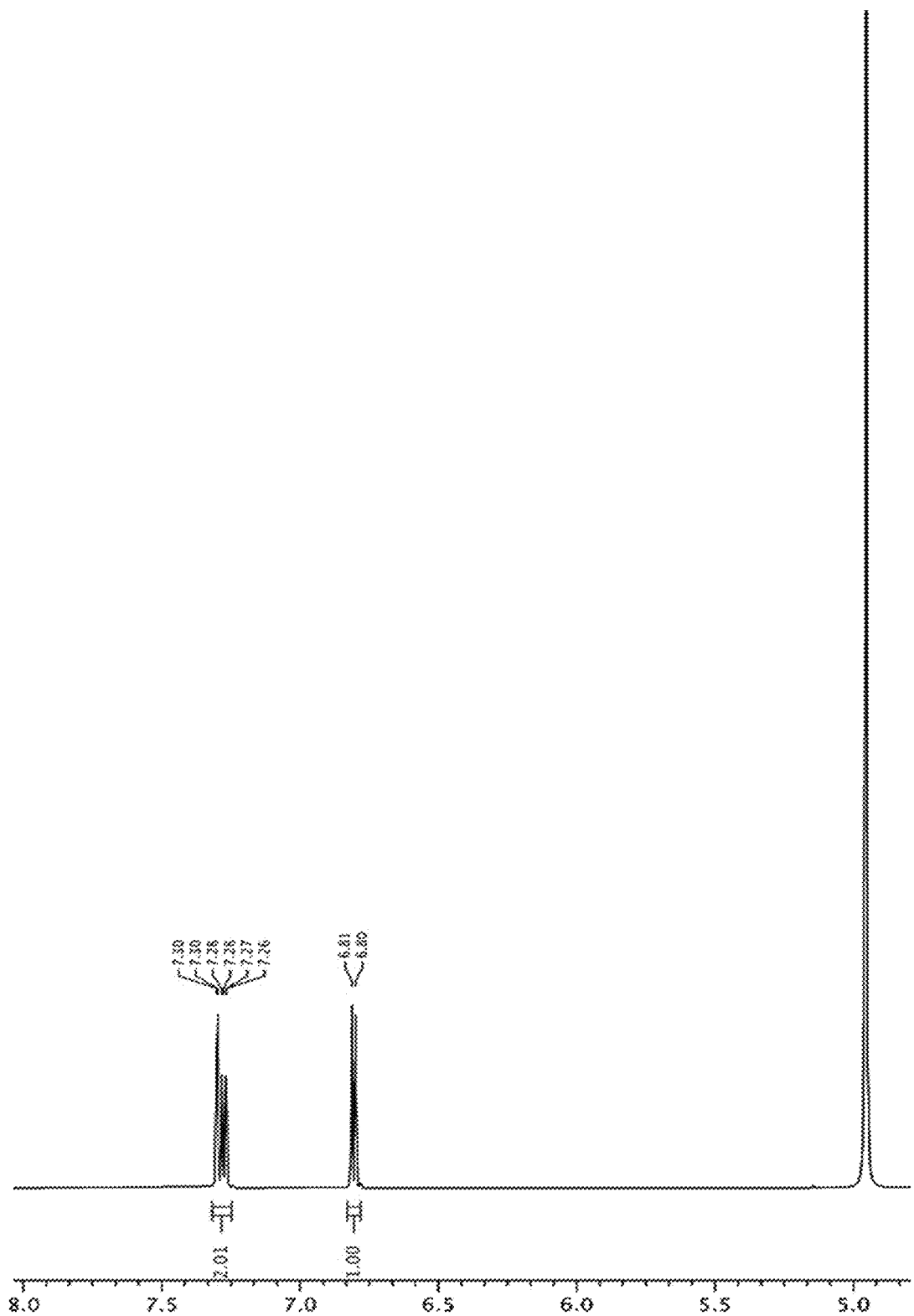
Figure 6B:
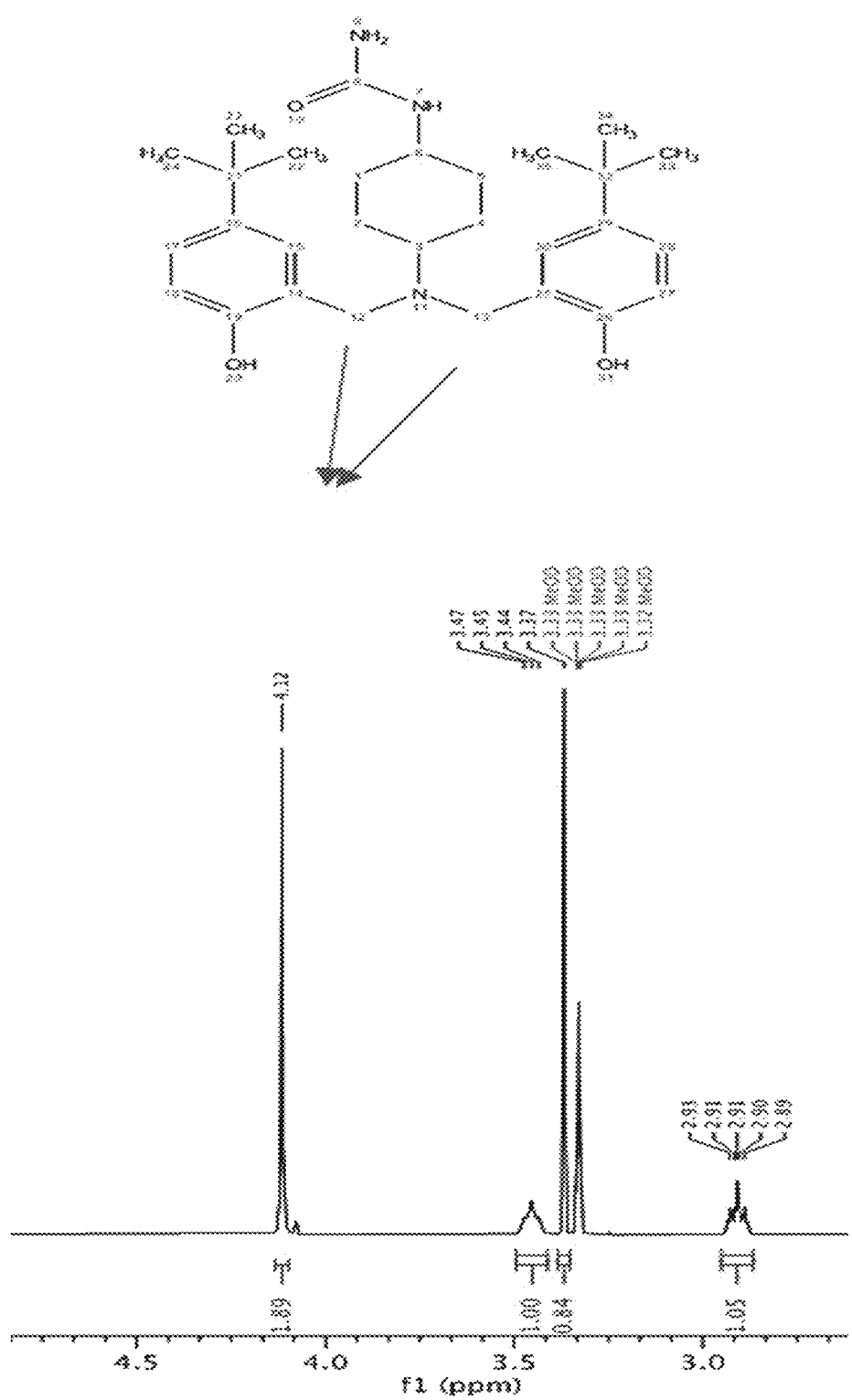

FIGS. 4A-4C show HPLC chromatograms of SZ-1 (FIG. 4A), SZ-2 (FIG. 4B), and SZ-3 (FIG. 4C). FIG. 5 shows the $^1$H NMR spectrum of the synthesized enamine SZ-1. FIGS. 6A-6B show $^{13}$C NMR attached proton test (APT) (FIG. 6A) and $^1$H NMR (FIG. 6B) spectra of the synthesized SZ-3.

Example II—SZ-3 as a Cofilin Inhibitor

Figure 7:
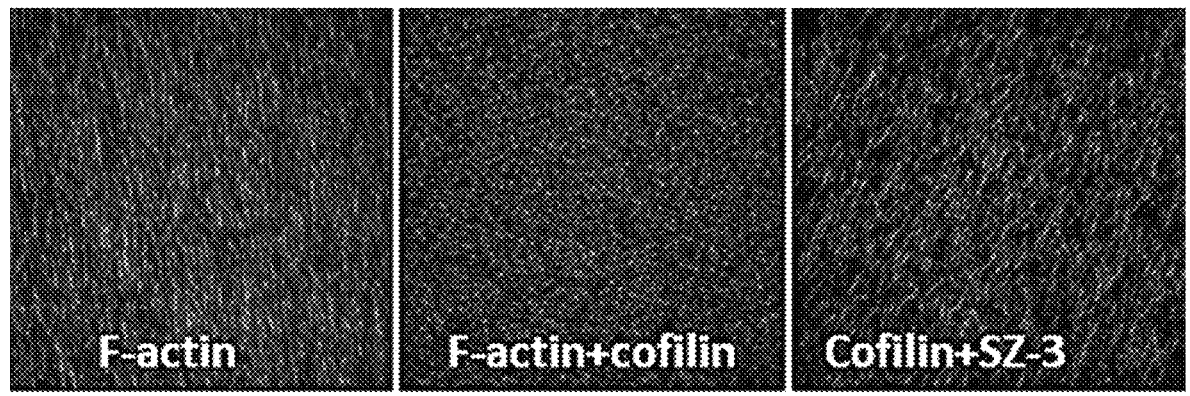
FIG. 7: F-actin depolymerizing assay showing that SZ-3 binds to cofilin. The inhibitory effect of SZ-3 was tested using an F-actin depolymerization assay. Rabbit muscle actin (Cytoskeleton, Inc.) was reconstituted with general actin and incubated on ice for 30 min to depolymerize any existing actin oligomers. Cofilin (Cytoskeleton, Inc.) at 0.25 μM and SZ-3 (5 μM) were added together to the corresponding vials and incubated for 30 min to ensure cofilin depolymerization and efficacy of the SZ-3. SiR-actin probe (Cytoskeleton, Inc.) was added at 50 nM and incubated for 1 h to visualize actin filaments. Finally, 5-10 μl of each group was added to a slide and imaged with fluorescent microscope at 652 nm. The control slide shows F-actin morphology (derived from rabbit muscle actin).

Evaluation of Cofilin Inhibition Activity Using in vitro F-actin Depolymerization Assay Cofilin inhibition with SZ-3 was tested using an f-actin depolymerization high-throughput screening assay. As per the endogenous severing and depolymerizing activity of cofilin, its addition to the F-actin resulted in severing and depolymerization of actin filaments. However, SZ-3 (5 μM) prevented the severing and depolymerizing activity of cofilin by efficiently binding to its binding site (FIG. 7).

Neuroprotective Properties of SZ-3

Figure 8A:
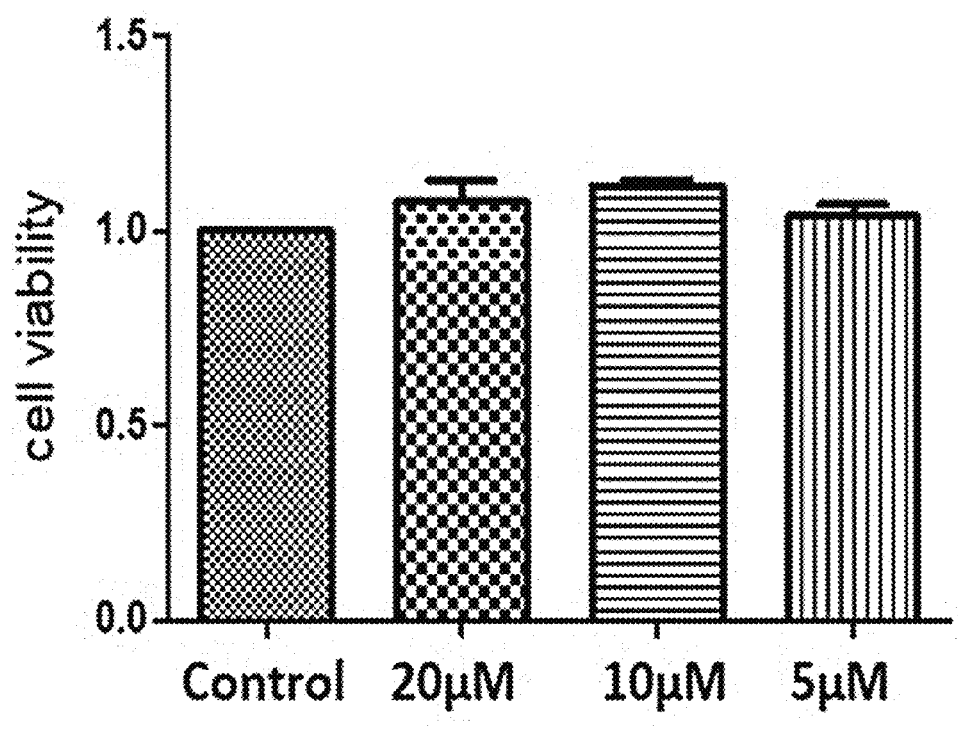
FIGS. 8A-8D: SZ-3 treatment protected SHSY cells from thrombin-induced cell death.
Figure 8B:
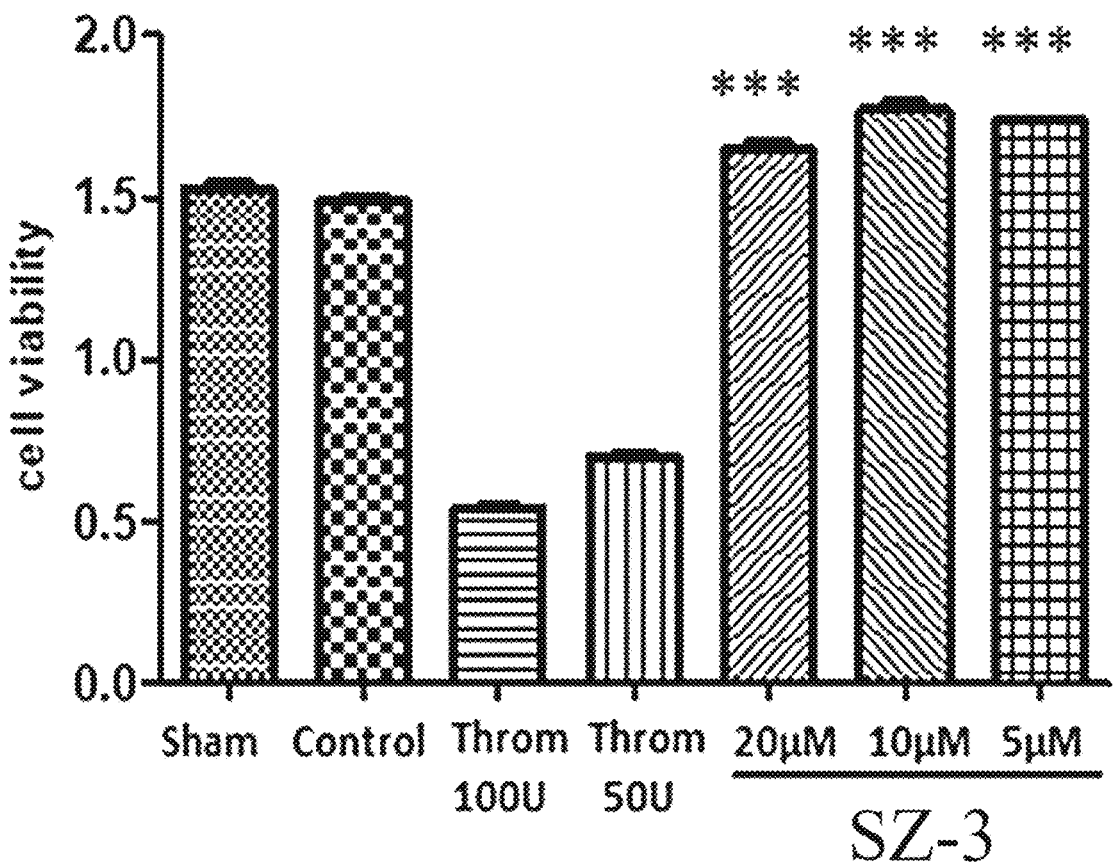
Figure 8C:
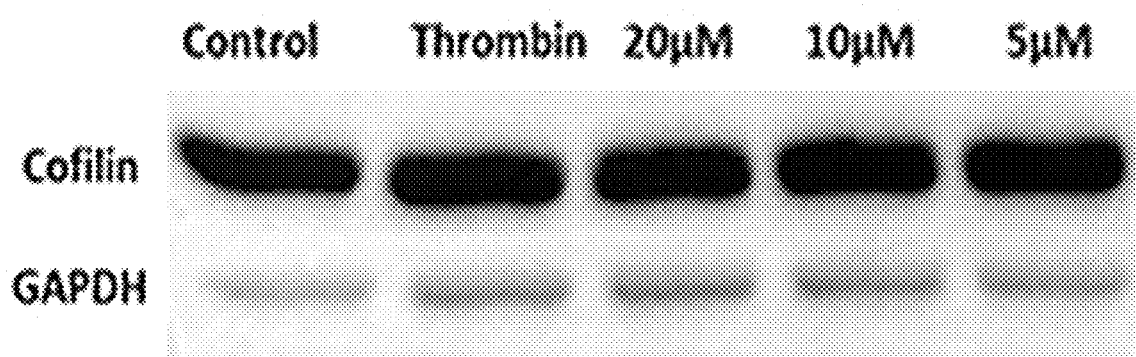
Figure 8D:
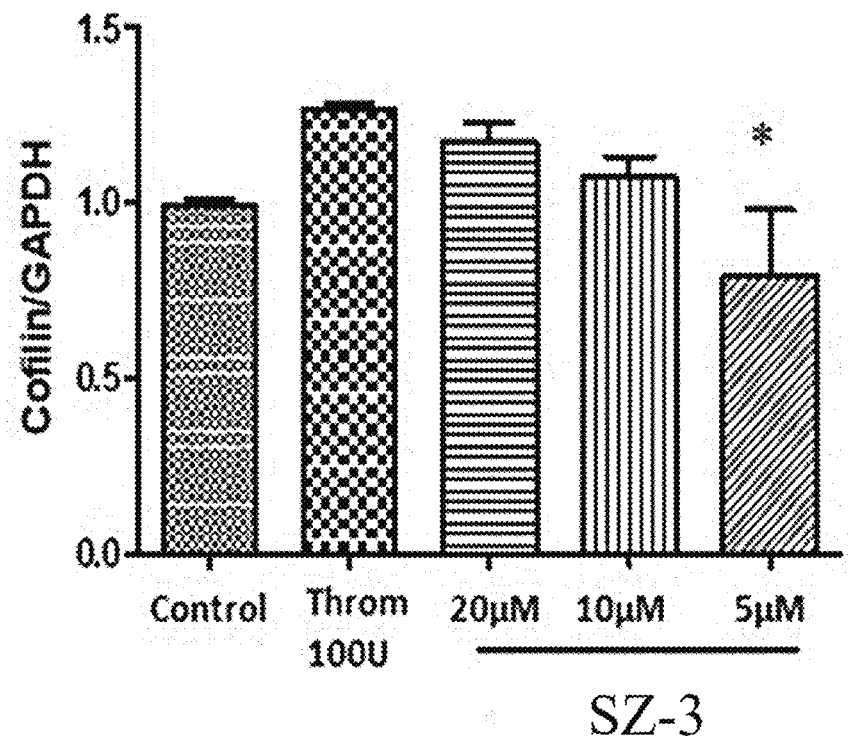
Figure 13:
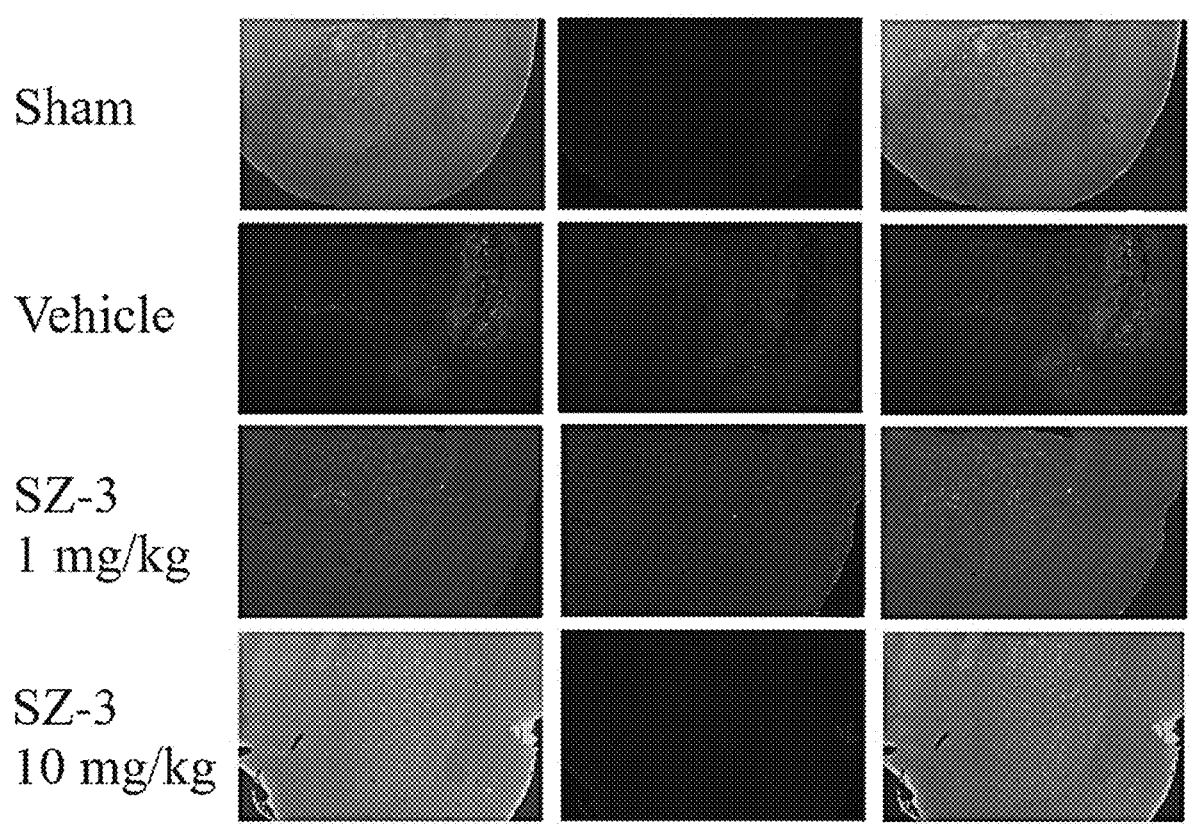
FIG. 13: SZ-3 reduces cell death after experimental ICH. The top column is Sham, the second column is vehicle, the third column is SZ-3 (1 mg/kg), and the fourth column is SZ-3 (10 mg/kg).

The synthesized SZ-3 compound was tested for neuroprotective properties in cell-based models using a neuroblastoma cell line (SHSY) and thrombin as a stressor. Thrombin was used as a cell death inducer in cell-based models for hemorrhagic brain injury. SHSY cells were challenged by 100 U/ml thrombin and after 3 hrs treated with different concentrations of synthesized compounds. SZ-3 did not show any signs of toxicity in SHSY cells when treated with different concentrations (FIG. 8A). In thrombin challenged and SZ-3 treated cells, SZ-3 significantly reversed the cell death with all three concentrations, with 10 μM showing the best effect (FIGS. 8B, 13). Cell death is observed through fluorescence. As seen in FIG. 13, there was a lot of cell death in the vehicle, and barely any cell death in the treatment with 10 μM SZ-3. As cofilin is the target here, its expression in thrombin-challenged SHSY cells was analyzed by WB analysis, and it was observed that SZ-3 treatment significantly reduced cofilin expression (FIG. 8C-8D).

SZ-3 Attenuates LPS-Induced Microglial Activation and Inflammation

Figure 9A:
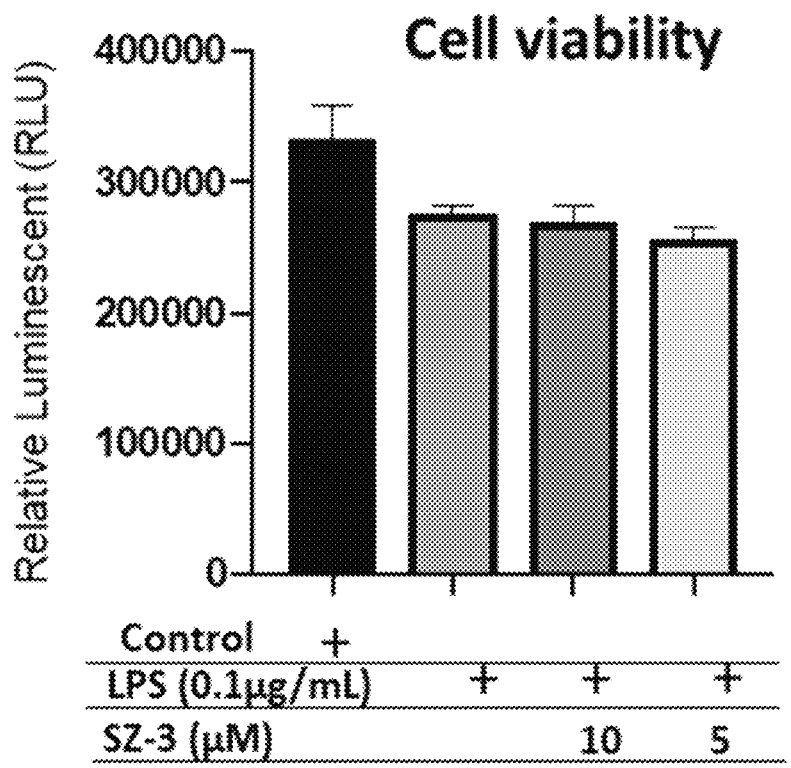
FIGS. 9A-9C: SZ-3 treatment reduced inflammatory cytokine release from microglial cells. Cultured HMC3 cells were challenged with 0.1 μg/mL of LPS and treated with different concentrations of SZ-3 concurrently. At the end of the experiment cells were harvested for MTT by CellTiter-Glo Luminescent assay (FIG. 9A), Griess assay for NO release (FIG. 9B), and TNF-α by ELISA (FIG. 9C). No toxicity was observed in 5-10 μM range of SZ-3. SZ-3 significantly reduced NO and TNF-α release from HMC3 cells after LPS treatment. These results are from 3 independent experiments using different cell cultures. *p<0.01, **p<0.001 relative to LPS group. *p<0.01 relative to control group.

After hemorrhage, activated microglia release proinflammatory mediators such as cytokines, chemokines, and nitric oxide (NO) leading to secondary injury which may be worse than the initial insult and may result in severe neurological deficits and death. In order to test whether the synthesized compound will reduce or stop microglial activation and inflammation after hemorrhage, whether the compound poses toxicity to microglia was first assessed. Human microglial cell line (HMC3) was challenged or activated with lipopolysaccharide (LPS) (0.1 μ/mL) and treated with different concentrations of the SZ-3 (10 and 5 μM) concurrently. CellTiter-Glo luminescent assay was used for cell viability; Griess reagent assay was used for NO release and ELISA was used for TNF-α estimations. No cell toxicity was observed in cells challenged with LPS and treated with SZ-3 (FIG. 9A).

Figure 9B:
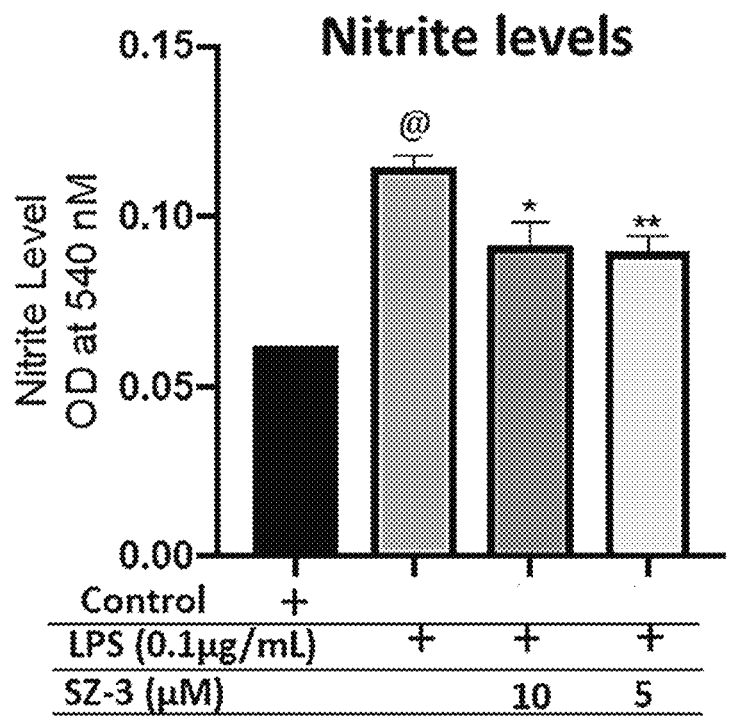
Figure 9C:
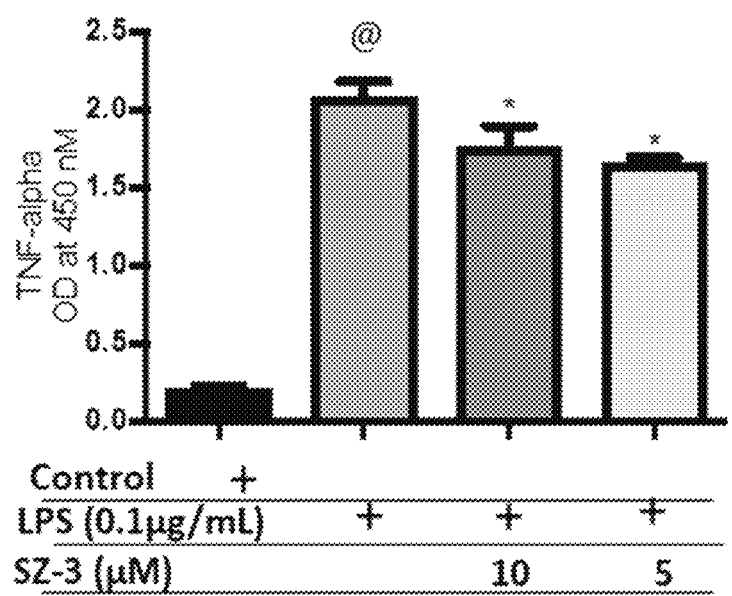

Next, a NO release assay was performed to determine if SZ-3 can reduce the NO release. When microglia were challenged with LPS, there was a significant increase in NO levels, demonstrating activation of microglia and converting into inflammatory phenotype. However, treatment with the SZ-3 (5 μM)-treated group significantly reduced NO release (p<0.001) as compared to control (non-treated) (FIG. 9B). SZ-3 (10 μM) significance was at p<0.01. Next, whether the major inflammatory cytokine TNF-α is reduced with the SZ-3 treatment was evaluated. As a consequence of microglial activation, TNF-α levels are increased, and the same pattern was observed when cells were challenged with LPS. There was a significant increase in TNF-α after LPS challenge. However, treatment with SZ-3 significantly reduced TNF-α levels in both 10 μM and 5 μM treatment groups compared to the non-treated control group (FIG. 9C).

SZ-3 Reduces Microglial Migration and Proliferation

Figure 10:
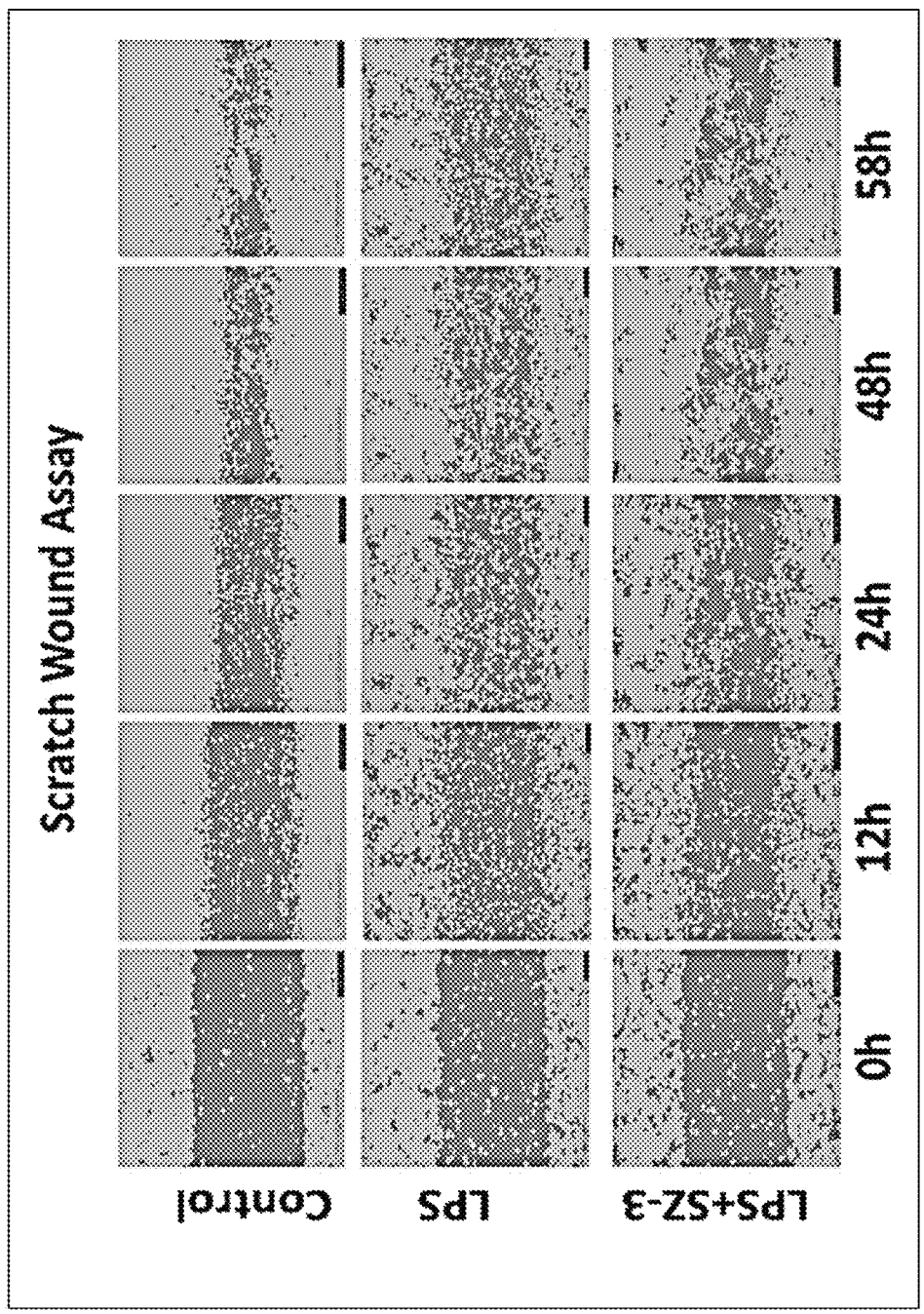
FIG. 10: SZ-3 treatment reduced microglial migration and proliferation. HMC3 cells were seeded onto a poly-D-lysine hydrobromidecoated-coated 96-well culture plate and placed overnight in a 37° C. IncuCyte S3. WoundMaker was used to simultaneously create wounds in all wells and then LPS (200 ng/ml) was added to wounded cells except control group. After 3 h cells were treated with DMSO (control) or SZ-3 (5 μM). The wound images were taken at 2 h intervals for 58 h. Data were processed and analyzed by using IncuCyte software.
Figure 10:
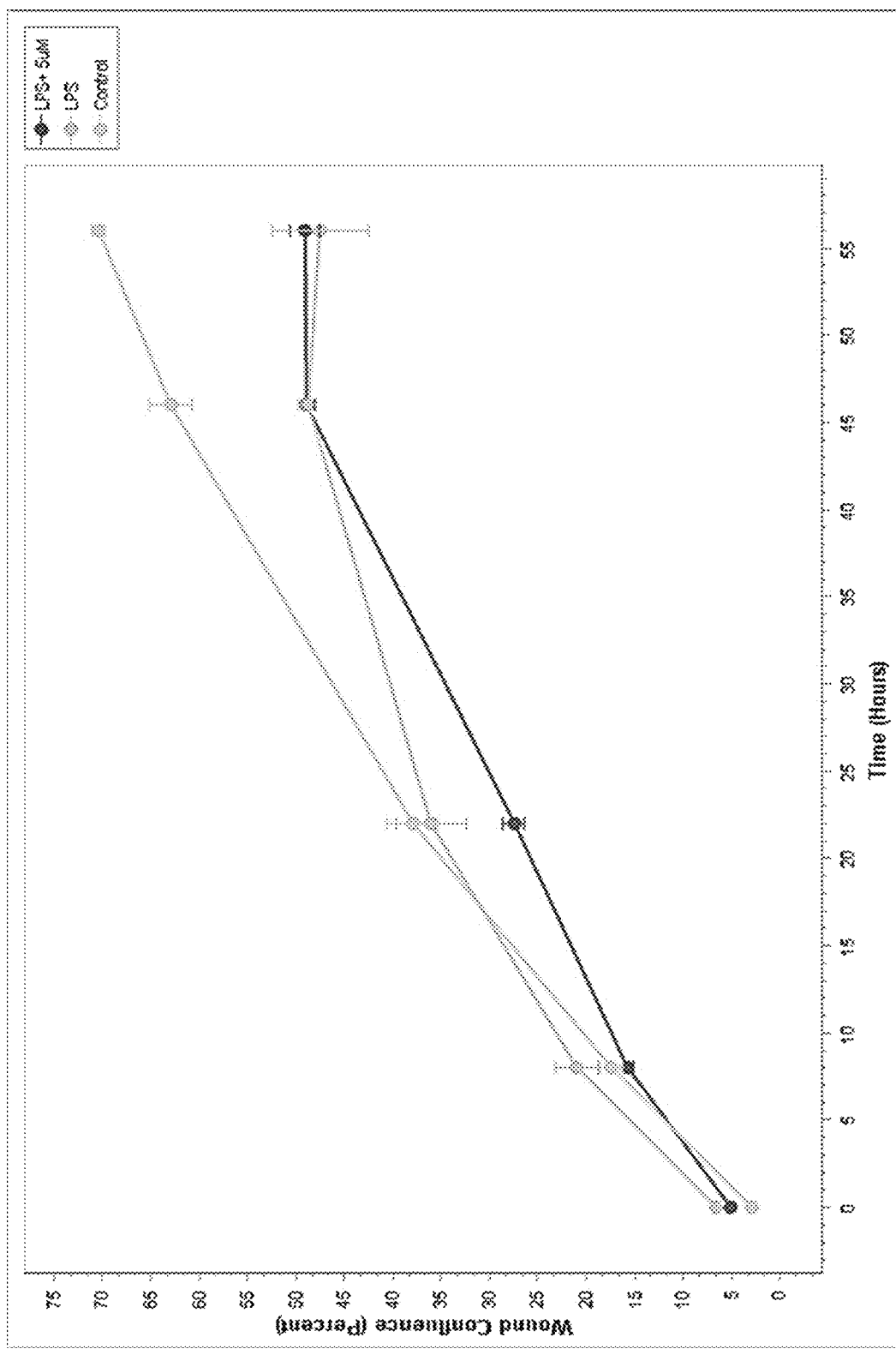
Figure 10:
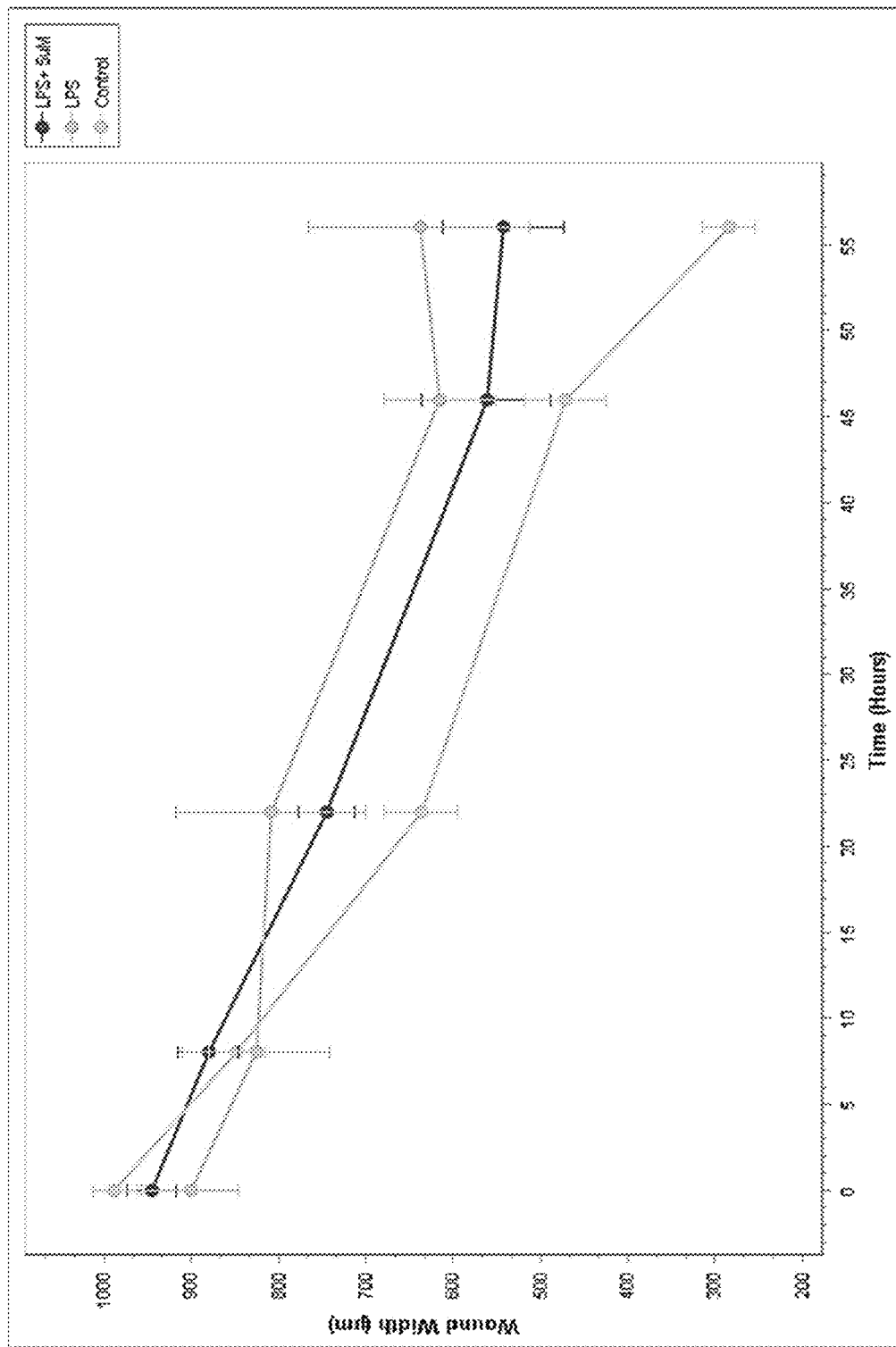
Figure 10:
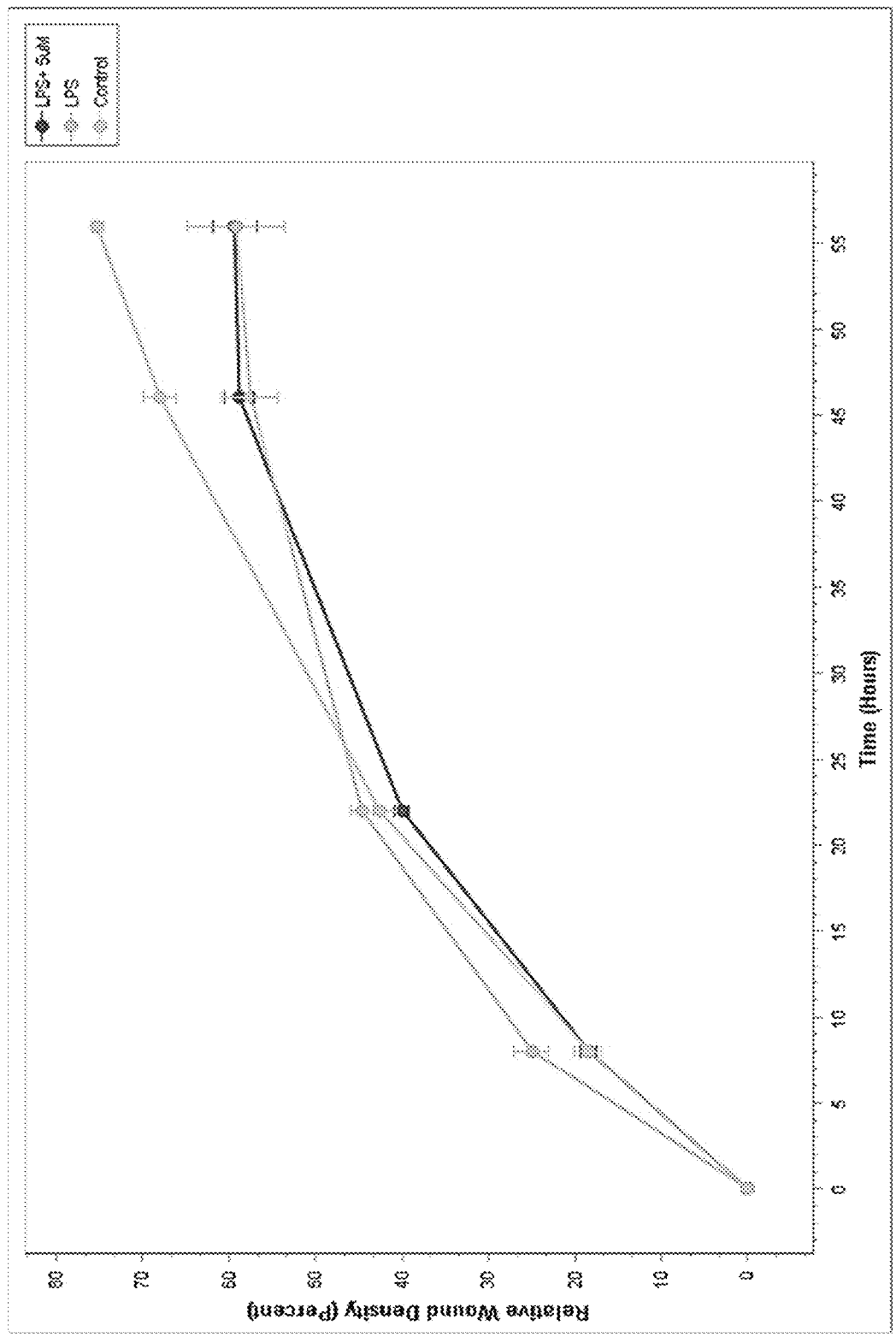

In response to brain injury, microglia transform into an activated state and migrate to the damaged area. This migration leads to an accumulation of activated microglia around the injury site resulting in vicious cycle of microglial activation and further release of inflammatory cytokines. To elucidate whether SZ-3 can stop or reduce the migration of activated microglial cells towards the injury site, a scratch wound assay was performed. At different time intervals, wound confluence, relative wound, and wound width metrics were assayed to analyze the migration of the microglial cells. The confluence of cells within the wound region was less with SZ-3 treated cells relative to non-treated cells in the first 24 h (FIG. 10A). Also, the distance between the migrating edges of the wound was significantly less in the control group compared with the LPS challenged group, and SZ-3 treated group was in between (FIG. 10B). Furthermore, the SZ-3 treated group had a slow increase rate in cell density in the wound area relative to the cell density outside of the wound area compared with the LPS challenged and control groups after the 24 h of treatment (FIG. 10C). These results demonstrate that SZ-3 reduces the proliferation and migration of the microglial cells toward the injury site.

Figure 11:
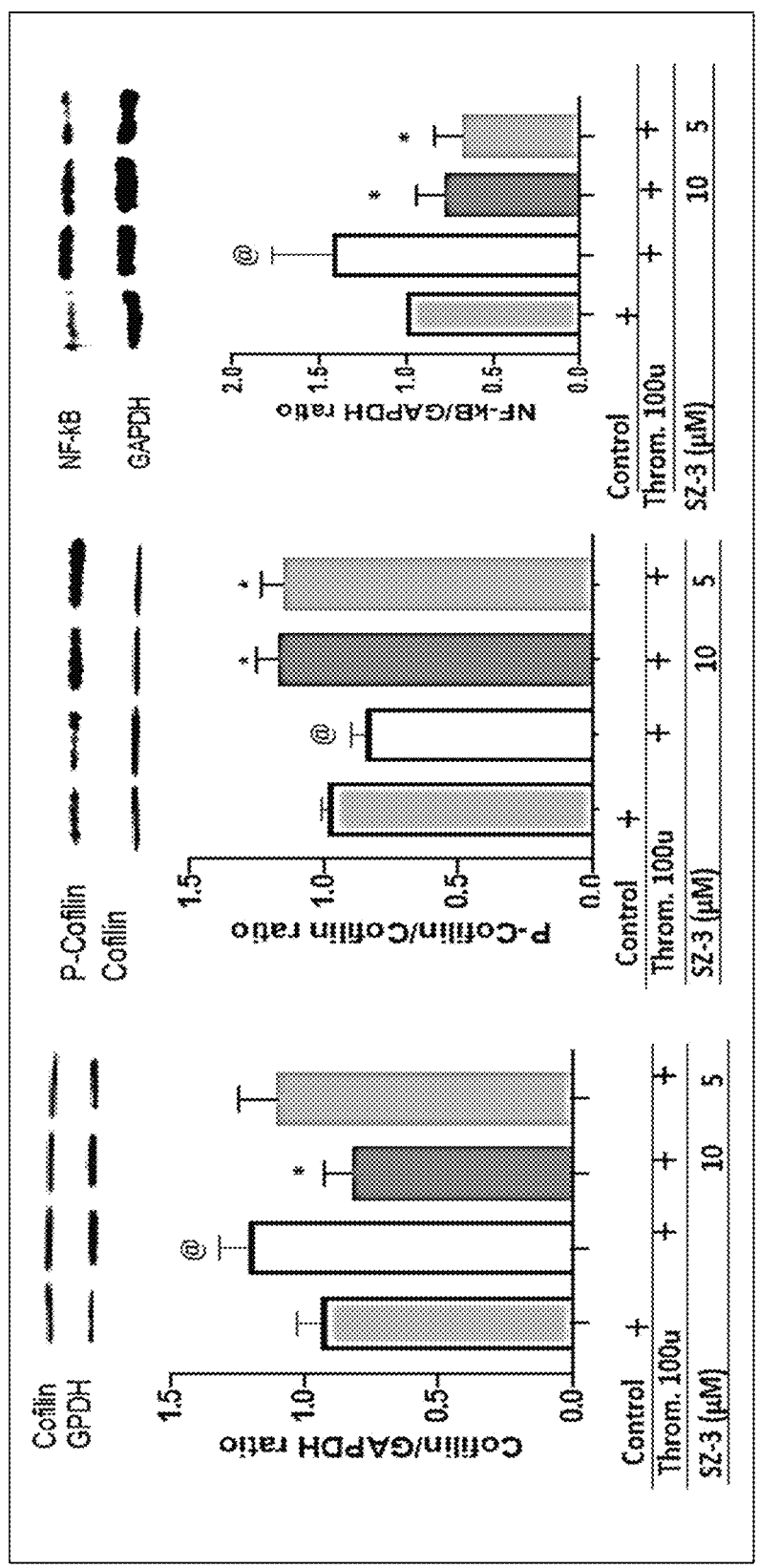
FIG. 11: SZ-3 reduces inflammation through NF-κB mechanism. Cultured HMC3 cells were challenged with thrombin 100 U/ml and after 3 h were treated with different concentrations of SZ-3 (10 and 5 μM). Cells were harvested for WB analysis after 24 h. The 10 μM concentration of SZ-3 significantly restored cell death induced by thrombin. WB analysis showed that cofilin expression was increased with thrombin exposure which was reduced by treatment with 5 μM of SZ-3. *p<0.01, ***p<0.0001 relative to thrombin group. These results are from 3 independent experiments using different cell cultures.

SZ-3 Inhibits Cofilin Overactivated Microglial Activation and Inflammation by NF-78 B Mechanism It has previously been shown that cofilin gene knockdown reduces microglial activation by reducing major inflammatory transcription factor NF-78 B. In order to show that SZ-3 also works through this mechanism, HMC3 cells were exposed to thrombin 100 U/ml and treated with ZS-3 (10, 5 μM) after 3 h followed by cell collection for WB after 24 h. WB was used to assay the expression levels of cofilin, phosphocofilin, and NF-κB. After thrombin challenge to HMC3 cells, a significant increase in cofilin and NF-78 B expression levels, which were significantly reduced in SZ-3 treatment groups, was observed. Nevertheless, a significant decrease in cofilin level was observed only in 10 μM of SZ-3 treatment group (FIG. 11). Phosphocofilin was observed to be decreased with thrombin treatment, and SZ-3 treatment reversed the expression levels. Without wishing to be bound by theory, the role of phosphocofilin is not fully understood, but it is believed that it is decreased in stress conditions and its restoration is beneficial.

Treatment with SZ-3 Improved Motor Deficits in Mice with Hemorrhage

Finally, it was desired to elucidate if treatment with SZ-3 can mitigate the hemorrhage induced behavioral deficits. Hemorrhage was induced in mice, and the mice were then treated with SZ-3. Mice were subjected to experimental hemorrhage by injecting collagenase into the mice striatum. Collagenase model simulates the hemorrhage by inducing vessel damage resulting in localized hematomas. This model is widely used in hemorrhagic stroke research.

Figure 12A:
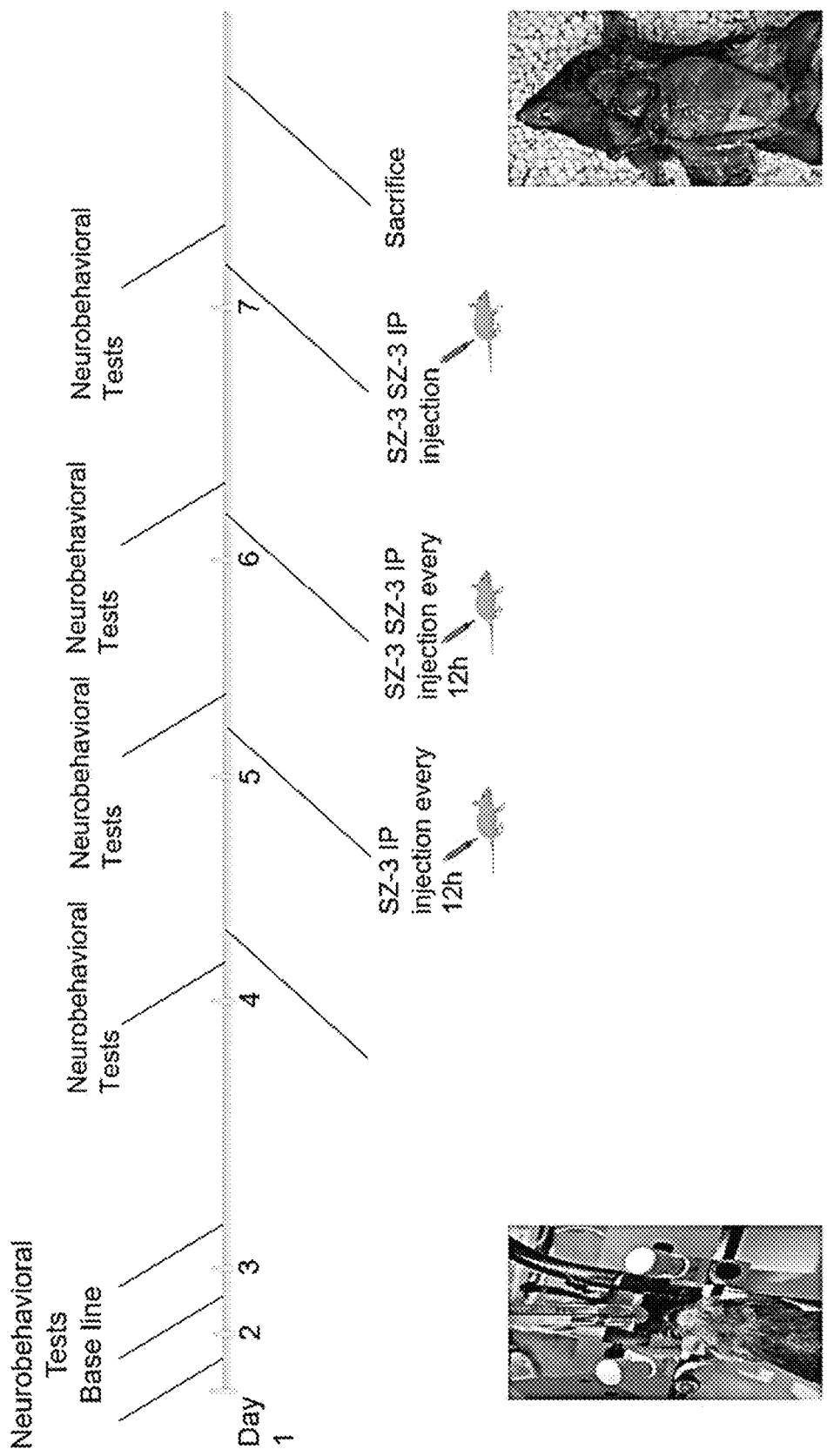
FIGS. 12A-12B: SZ-3 treated mice showed enhanced recovery after hemorrhage. Mice were subjected to experimental hemorrhage by injecting collagenase into the striatum. After 3 h of collagenase injection, mice were treated with two concentrations of SZ-3 (1 and 10 mg/kg, i.p.) followed by 12 hourly injections until day 3. Mice were evaluated for baseline rotarod and grip strength 24 h prior and after hemorrhage and then after every 24 hs for three days. N=12 per group.
Figure 12B:
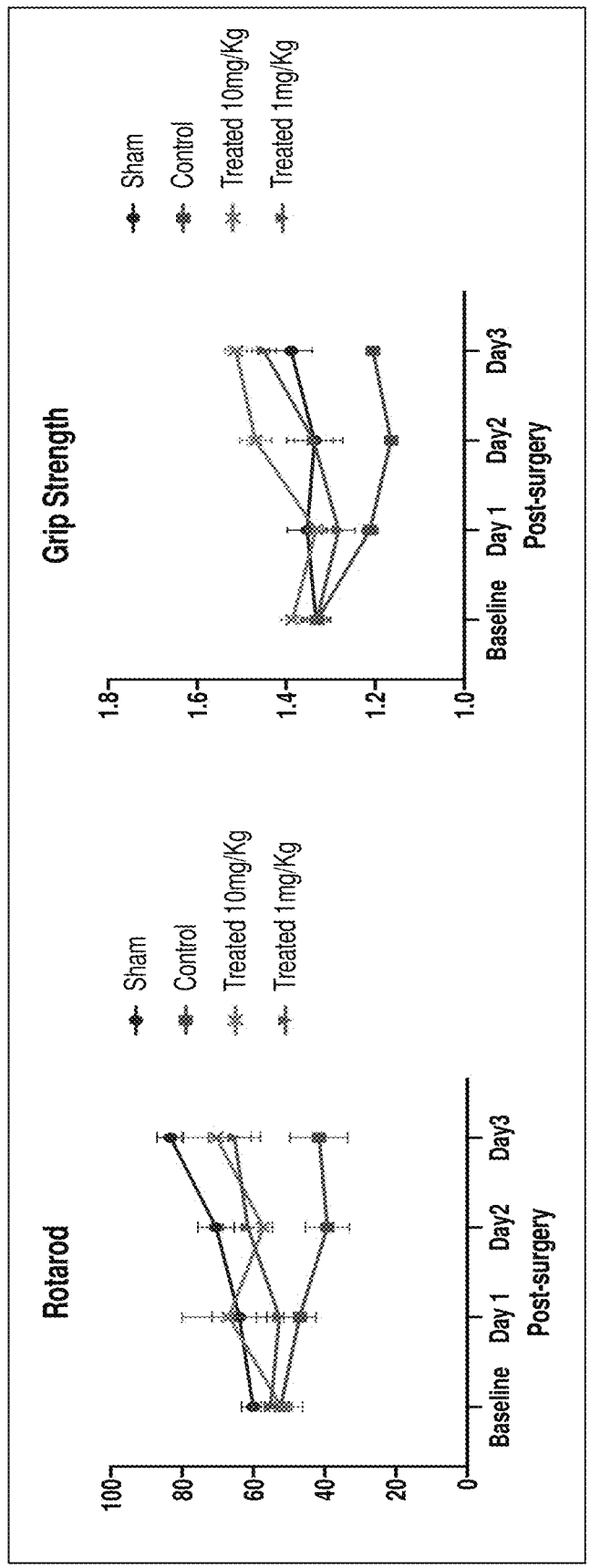

Mice were treated with two concentrations of SZ-3 (1 and 10 mg/kg, i.p;) immediately after 3 h of hemorrhage and then after every 12 h for 3 days (FIG. 12A). A significant drop in motor function assessed by rotarod was observed at day 2 and 3, which was significantly reversed with the SZ-3 treatment, with both concentrations showing similar effect. Normally, the mice are substantially paralyzed a short time after the stroke. Control mice (having induced hemorrhage without treatment) suffered from grip strength impairment after 24 h of hemorrhage and mice treated with SZ-3 showed enhanced grip strength (FIG. 12B). Thus, motor activity increased in the mice with the SZ-3 treatment. These results indicate that SZ-3 not only restores inflammation but also improves recovery after hemorrhagic stroke.

Sham mice had no induced hemorrhage or treatment. Important, treatment of sham mice with SZ-3 showed improvement. The treatment with SZ-3 improved the grip of the mice even without hemorrhage first. Thus, SZ-3 may be used to improve motor function and muscle strength.

Furthermore, no lesions formed in the mice, and there were no solubility issues with SZ-3. This indicates that SZ-3 is both safe and practical for use as a drug.

Methods

Scratch Wound Assay

HMC3 cells (30,000 cells/well) were seeded onto a poly-D-lysine hydrobromidecoated-coated 96-well culture plate (corning) and placed overnight in a 37° C. IncuCyte S3 (Essen BioScience) supplied with 5% $CO_2$. WoundMaker (Essen BioScience) was used to simultaneously create wounds in all wells then washed twice with culture medium. LPS (200 ng/ml) was added to wounded cells except control group immediately after the wash. 3 h later cells were treated with DMSO (control) or SZ-3 (5 μM). The wound images were taken at 2 h intervals for 72 h. Data were processed and analyzed by using IncuCyte software.

Cell Cultures

HMC3 cells were cultured in DMEM/F12 medium supplemented with 5% horse serum (HS), 10% fetal bovine serum (FBS), and 1% penicillin/streptomycin. Cells were stimulated with 100 U/ml thrombin from bovine plasma (Sigma) and treated without (vehicle) or with different concentrations of SZ-3.

Western Blotting Analysis

Cells were harvested and washed with ice-cold lysis buffer (250 mM sucrose, 1.5 mM $MgCl_2$, 10 mM KCl, 20 mM HEPES 7.6 pH, 1 mM of dithiothreitol, 1 mM phenylmethylsulfonyl fluoride, 50 mM NaF, 10 mM sodium orthovanadate, 20 mM sodium pyrophosphate, and protease inhibitors) for 15 min then supplemented with 5% of Nonidet P-40 for 2 min. Cytosolic fraction was collected from the supernatant after centrifugation at 14,000 g for 10 min. Bradford reagent (Bio-Rad Laboratories) was used to determine the protein concentrations, and equal amounts of samples were loaded onto 10-15% SDS-polyacrylamide gels, separated by electrophoresis, and transferred to PVDF membranes. Membranes were blocked and incubated with primary antibodies; cofilin, phosphocofilin, and NF-kB (Cell Signaling Technology) at 4° C. overnight. Membranes were incubated for 1 h at room temperature with horseradish peroxidase-conjugated secondary antibody (1:5000; Jackson ImmunoResearch) after washing. Glyceraldehyde 3-phosphate dehydrogenase (GAPDH) or beta-actin were used as the loading control, and band intensity analyzed using Bio-Rad Chemi-Doc XRS Image Lab Software.

Cell Proliferation and Viability Assay

All types of cells used in these examples were assayed for viability and proliferation after 24-72 h using the MTT or CellTiter-Glo Luminescent assay Promega (Madison, Wis.). Cells after treatment were incubated with MTT reagent for 3 h in 5% $CO_2$ at 37° C. The medium was replaced with DMSO to dissolve formazan crystals. Absorbance was read at 570 nm to quantify cell viability. CellTiter-Glo reagents were used in some experiments by adding equal amounts of reagent to the amount of medium containing cells for a 96-well plate. Contents were mixed for 2 minutes then incubated the plate for 10 minutes at room temperature to stabilize luminescent signal.

Nitrite Assay

NO was indirectly assayed through the measurement of nitrite by mixing a sample of culture medium with an equal volume of Griess reagent (0.3% naphthylethylenediamine dihydrochloride, 3% sulfanilamide, 8% phosphoric acid) and reading at 540 nm.

ELISA Assay

HMC3 cells (30,000 cells/well in a 96-well plate) were stimulated by LPS (1 μg/ml), then treated with DMSO or different concentrations of drug 3 h later. The supernatants were collected after 24 h, and the concentrations of TNF-α were measured using enzyme-linked immunosorbent assay (ELISA) according to the kit's instructions (R&D Systems, Inc.).

Evaluation of SZ-3 Activity Using in vitro F-actin Depolymerization Assay

SZ-3 inhibitory effect on cofilin was tested using F-actin depolymerization assay. Briefly, rabbit muscle actin (Cytoskeleton, Inc.) was reconstituted with general actin buffer to 40 μM (stock) and incubated on ice for 30 min to depolymerize any existing actin oligomers. Next, actin stock solution was further diluted to a 1 μM working solution and then polymerized into filaments with the addition of 1/10 th the volume of actin polymerization buffer (Cytoskeleton, Inc.). The mix was incubated at room temperature for 1 h to ensure optimum polymerization. Next, F-actin solution was aliquoted into 6 vials representing control (vehicle), cofilin, SZ-3 (5 μM), SZ-3 (10 μM), Cofilin+SZ-3 (10 μM), and Cofilin+SZ-3 (5 uM) groups. Then cofilin (Cytoskeleton, Inc.) at 0.25 μM and SZ-3 were added together to the corresponding vials and incubated for 30 minutes to ensure cofilin depolymerization. Next, SiR-Actin probe (Cytoskeleton, Inc.) was added at 50 nM and incubated for 1 h to visualize actin filaments. Finally, 5-10 μl of each group was added to a slide, coverslipped, and imaged with fluorescent microscope at 652 nm.

Certain embodiments of the compositions, compounds, and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A compound of Formula I:

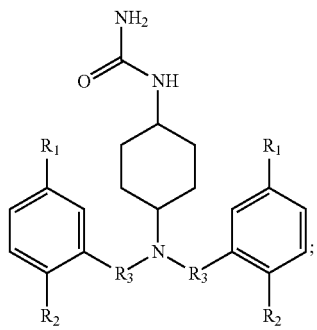

Formula I wherein:

each $R_1$ is independently H or a hydrophobic group;

each $R_2$ is independently H, a hydrophilic group, or a protecting group; and each $R_3$ is independently $(CH_2)_n$, where n is an integer from 1 to 10;

or a racemate, hydrate, solvate, stereoisomer, polymorph, or prodrug thereof.

2. The compound of claim 1, wherein each $R_1$ is independently selected from the group consisting of H and tert-butyl.

3. The compound of claim 1, wherein each $R_2$ is independently selected from the group consisting of H and OH.

4. The compound of claim 1, wherein each $R_1$ is independently selected from the group consisting of H and tert-butyl, and each $R_2$ is independently selected from the group consisting of H and OH.

5. The compound of claim 1, wherein at least one $R_2$ comprises a tert-butyldimethyl silyl protecting group.

6. The compound of claim 1, wherein the compound is SZ-3:

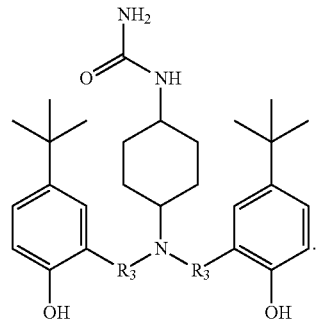

(SZ-3)

7. The compound of claim 1, wherein the compound is a prodrug of SZ-3:

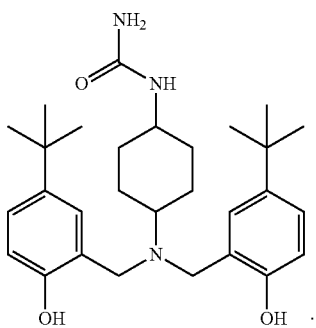

8. The compound of claim 1, wherein the compound is SZ-2:

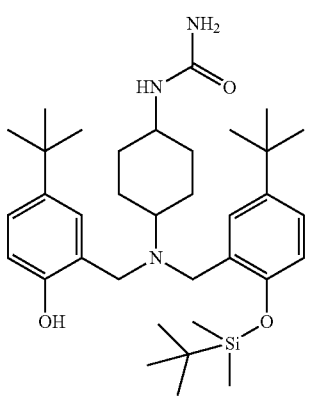

9. The compound of claim 1, wherein each $R_3$ is independently selected from the group consisting of —CH$_2$—, —CH$_2$CH$_2$—, and —CH$_2$CH$_2$CH$_2$—.

10. A composition comprising the compound of claim 1 and a pharmaceutically acceptable carrier, diluent, or adjuvant.

11. A method of inhibiting cofilin activity or reducing total cofilin, the method comprising administering an effective amount of a small molecule to a subject and inhibiting cofilin activity or reducing total cofilin in the subject, wherein the small molecule is a compound of Formula I:

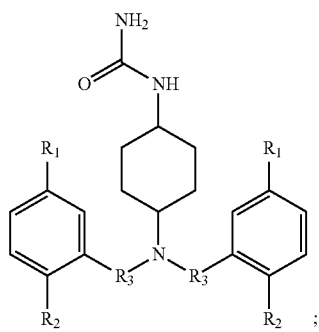

wherein:
each $R_1$ is independently H or a hydrophobic group;
each $R_2$ is independently H, a hydrophilic group, or a protecting group; and each $R_3$ is independently (CH$_2$)$_n$, where n is an integer from 1 to 10;

or a racemate, hydrate, solvate, stereoisomer, polymorph, or prodrug thereof.

12. The method of claim 11, wherein the small molecule is SZ-3:

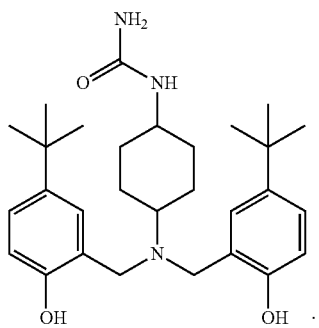

13. The method of claim 11, wherein the small molecule is SZ-2:

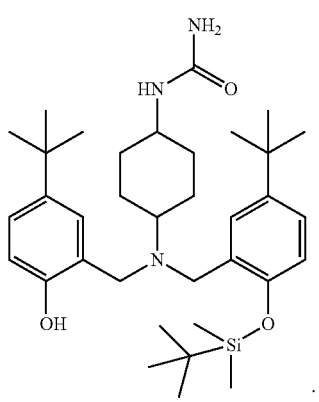

14. A method of treating hemorrhagic brain injury-induced neuroinflammation, the method comprising administering to a subject having a hemorrhagic brain injury an effective amount of a compound, and treating hemorrhagic brain injury-induced neuroinflammation in the subject, wherein the compound is a compound of Formula I:

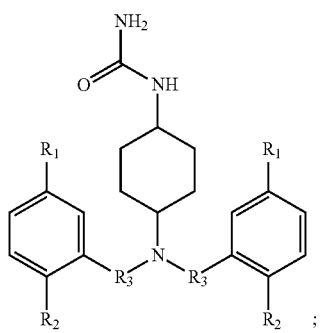

wherein:
  each $R_1$ is independently H or a hydrophobic group;
  each $R_2$ is independently H, a hydrophilic group, or a protecting group; and
  each $R_3$ is independently $(CH_2)_n$, where n is an integer from 1 to 10;
or a racemate, hydrate, solvate, stereoisomer, polymorph, or prodrug thereof.

15. The method of claim 14, wherein the compound is SZ-3:

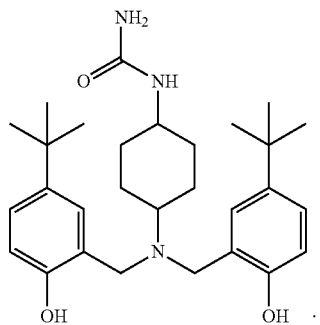

(SZ-3)

16. The method of claim 14, wherein the compound is SZ-2:

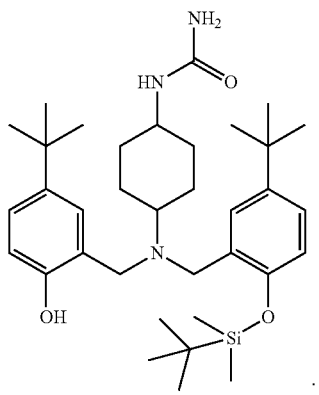

(SZ-2)

* * * * *

UNITED STATES PATENT AND TRADEMARK OFFICE
CERTIFICATE OF CORRECTION

PATENT NO. : 11,548,850 B2  
APPLICATION NO. : 16/867100  
DATED : January 10, 2023  
INVENTOR(S) : Saleh Alaqel, Viranga Tillekeratne and Zahoor Shah It is certified that error appears in the above-identified patent and that said Letters Patent is hereby corrected as shown below:

In the Claims

Column 24, Claim 6, Line 50-65, please correct:

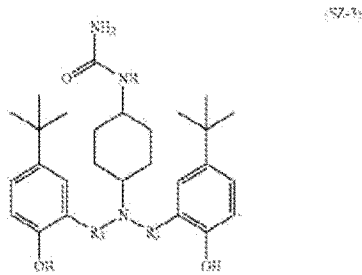

To:

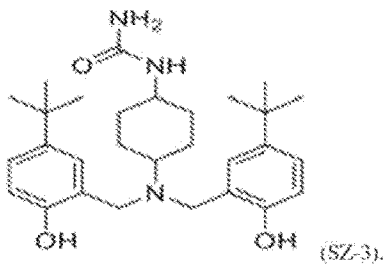

Signed and Sealed this  
Second Day of May, 2023

Katherine Kelly Vidal  
*Director of the United States Patent and Trademark Office*